United States Patent
Bourquin et al.

(10) Patent No.: US 11,896,301 B2
(45) Date of Patent: Feb. 13, 2024

(54) HANDHELD DEVICE FOR PERFORMING A TREATMENT OPERATION ON SKIN

(71) Applicant: KONINKLIJKE PHILIPS N.V., Eindhoven (NL)

(72) Inventors: Yannyk Parulian Julian Bourquin, Eindhoven (NL); Jonathan Alambra Palero, Waalre (NL); Bastiaan Wilhelmus Maria Moeskops, Uden (NL); Kiran Kumar Thumma, Eindhoven (NL); Frank Anton Van Abeelen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 426 days.

(21) Appl. No.: 17/263,181

(22) PCT Filed: Aug. 21, 2019

(86) PCT No.: PCT/EP2019/072318
§ 371 (c)(1),
(2) Date: Jan. 26, 2021

(87) PCT Pub. No.: WO2020/038970
PCT Pub. Date: Feb. 27, 2020

(65) Prior Publication Data
US 2021/0322098 A1     Oct. 21, 2021

(30) Foreign Application Priority Data
Aug. 21, 2018   (EP) ..................................... 18189856

(51) Int. Cl.
*A61B 18/20*     (2006.01)
*A61B 5/0531*     (2021.01)
(Continued)

(52) U.S. Cl.
CPC ............ *A61B 18/20* (2013.01); *A61B 5/0531* (2013.01); *A61B 5/441* (2013.01);
(Continued)

(58) Field of Classification Search
CPC ............ A61B 2018/00648; A61B 2018/00904
See application file for complete search history.

(56) References Cited

U.S. PATENT DOCUMENTS 6,280,438 B1   8/2001   Eckhouse
9,308,391 B2   4/2016   Liu
(Continued)

OTHER PUBLICATIONS

International Search Report and Written Opinion dated Oct. 11, 2019 for International Application No. PCT/EP2019/072318 Filed Aug. 21, 2019.
(Continued)

*Primary Examiner* — James M Kish
*Assistant Examiner* — Jessica L Mullins

(57) ABSTRACT

According to an aspect, there is provided a handheld device (2) for applying energy pulses to skin (17) of a subject to perform a treatment operation as the handheld device is moved across the skin, the handheld device comprising: an aperture (6) that is to be placed adjacent to the skin; at least one energy source (8) for generating an energy pulse and for providing the energy pulse through the aperture to perform the treatment operation on 5 skin adjacent the aperture, wherein the at least one energy source has a minimum pulse repetition period following the generation of an energy pulse before a subsequent energy pulse can be generated; a first skin property sensor (14) for measuring a skin property and for outputting a first measurement signal representing measurements of the skin property at a first sensing position (24), wherein the skin property is a property that changes in response to the application of an energy pulse to the skin, (Continued)

and wherein the first sensing position is in front of the aperture relative to an intended motion direction of the handheld device over the skin; a second skin property sensor (16) for measuring the skin property and for outputting a second measurement signal representing measurements of the skin property at a second sensing position (26), wherein the second sensing position is behind the aperture relative to the intended motion direction; a memory unit (56); and a control unit (10) that is coupled to the at least one energy source to control the generation of energy pulses by the at least one energy source, and coupled to the first skin property sensor and the second skin property sensor to obtain the first measurement signal and the second measurement signal, wherein the control unit is configured to store a profile of at least the first measurement signal in the memory unit; wherein the control unit is further configured to, when the handheld device is moving in the intended motion direction over the skin: analyse the profile of the first measurement signal to determine if the first skin property sensor is passing over a previously treated area of skin; on detecting that the first skin property sensor is not passing over a previously treated area of skin, control the at least one energy source to generate an energy pulse if, or once, the minimum pulse repetition period following the generation of a previous energy pulse has expired; on detecting that the first skin property sensor is passing over a previously treated area of skin, performing the consecutive operations of: preventing the generation of an energy pulse, even if the minimum pulse repetition period following the generation of a previous energy pulse has expired; marking a point in the profile of the first measurement signal stored in the memory unit according to a predetermined rule, wherein the marked point relates to a position on the previously treated area of skin; using information about the marked point, analyse the profile of the second measurement signal to identify a similar marked point in the profile of the second measurement signal; on identifying the similar marked point in the profile of the second measurement signal, controlling the at least one energy source to generate an energy pulse if, or once, the minimum pulse repetition period following the generation of a previous energy pulse has expired.

20 Claims, 12 Drawing Sheets

(51) Int. Cl.
 *A61B 5/00* (2006.01)
 *A61B 18/00* (2006.01)
(52) U.S. Cl.
 CPC .............. *A61B 2018/00476* (2013.01); *A61B 2018/00648* (2013.01); *A61B 2018/00797* (2013.01); *A61B 2018/00875* (2013.01); *A61B 2018/00904* (2013.01); *A61B 2018/00922* (2013.01); *A61B 2018/202* (2013.01)

(56) References Cited

U.S. PATENT DOCUMENTS

| | | |
|---|---|---|
| 2002/0173781 A1 | 11/2002 | Cense |
| 2006/0247740 A1 | 11/2006 | Roersma |
| 2008/0262484 A1 | 10/2008 | Hawkins |
| 2009/0210037 A1 | 8/2009 | Roersma |
| 2011/0004201 A1 | 1/2011 | Nuijs |
| 2014/0005756 A1 | 1/2014 | Liu |
| 2015/0230863 A1 | 8/2015 | Youngquist |
| 2015/0366611 A1 | 12/2015 | Rosenberg |
| 2016/0045762 A1 | 2/2016 | Gurovich |
| 2016/0250497 A1 | 9/2016 | Jay |
| 2016/0374758 A1 | 12/2016 | Jones |
| 2017/0215958 A1 | 8/2017 | Beerwerth |

OTHER PUBLICATIONS

International Preliminary Report on Patentability dated Apr. 1, 2020 for International Application No. PCT/EP2019/072318 Filed Aug. 21, 2019.

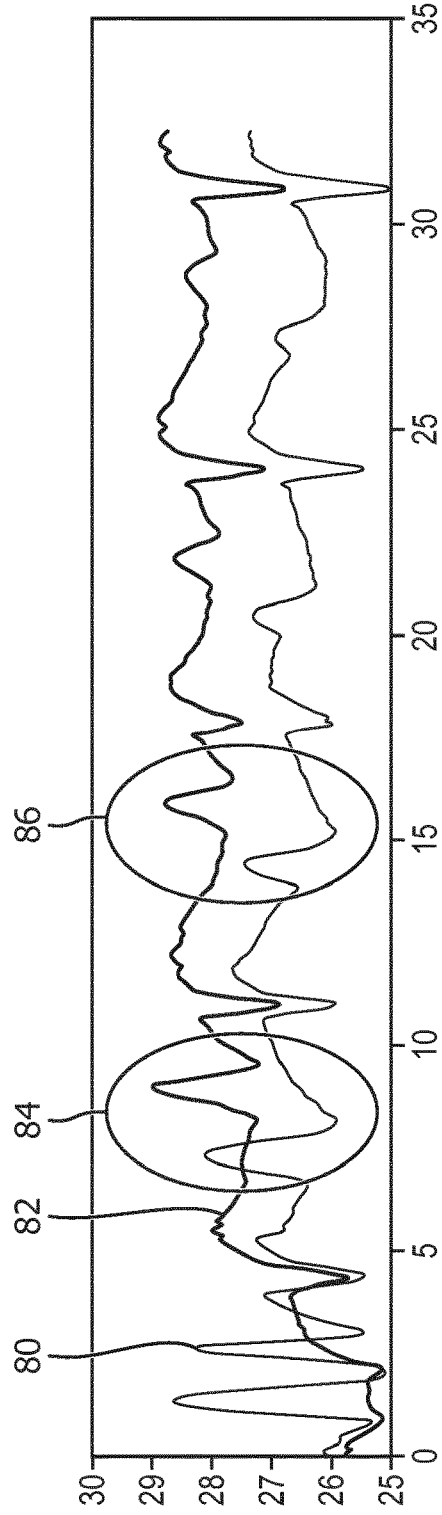
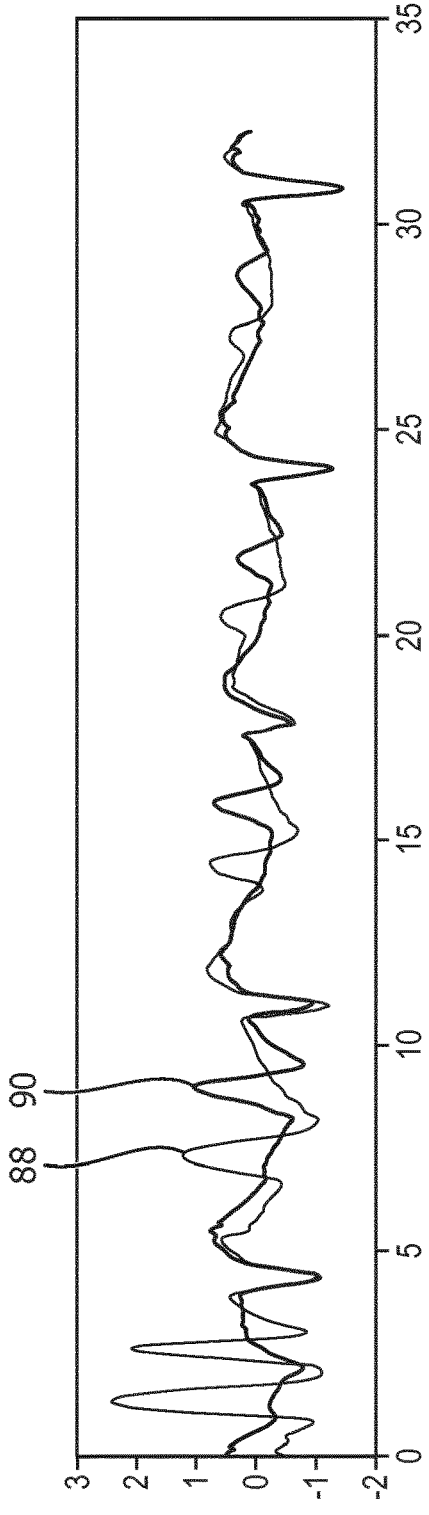
FIG. 7a
FIG. 7b

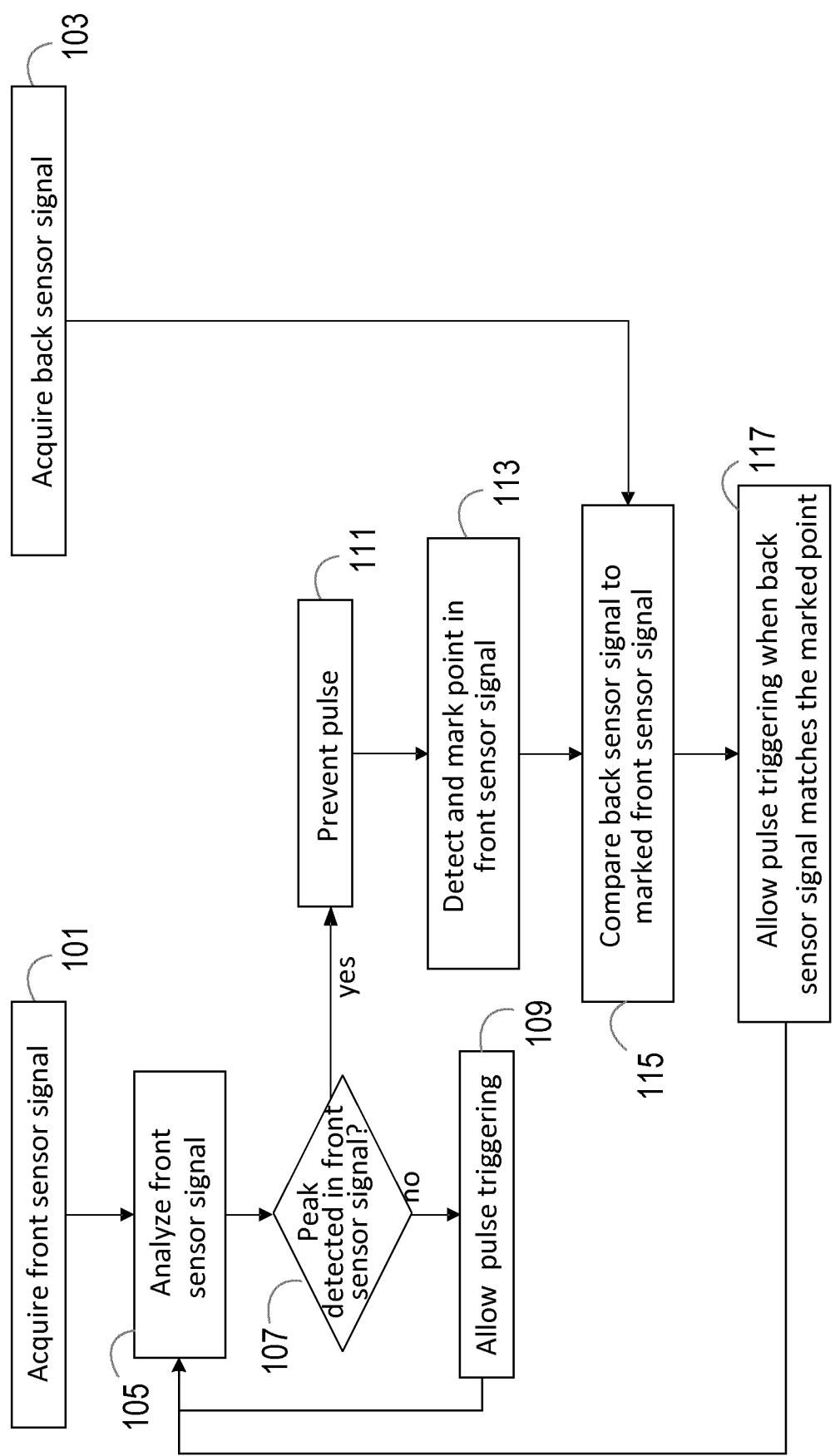

HANDHELD DEVICE FOR PERFORMING A TREATMENT OPERATION ON SKIN

CROSS REFERENCE TO RELATED APPLICATIONS

This application is the U.S. National Phase application under 35 U.S.C. § 371 of International Application No. PCT/EP2019/072318 filed Aug. 21, 2019, which claims the benefit of European Patent Application Number 18189856.0 filed Aug. 21, 2018. These applications are hereby incorporated by reference herein.

FIELD OF THE INVENTION

This disclosure relates to a handheld device for performing a treatment operation on skin of a subject, and in particular to a treatment operation in which energy pulses are applied to the skin.

BACKGROUND OF THE INVENTION

Techniques for removal of unwanted hairs include shaving, electrolysis, plucking, laser and light therapies (known as photoepilation) and injection of therapeutic anti-androgens. Light-based technologies are also used in other types of dermatological treatments, including hair growth reduction and treating acne.

Through the use of an appropriate configuration of the light energy, i.e. in terms of wavelength, intensity and/or pulse duration, selective heating of the hair root and subsequent temporary or permanent damage to the hair follicle can be achieved. However, due to the high fluence required to achieve sufficient temperature elevation in the follicle, the energy consumption of devices that provide these energy pulses can be very high. This negatively affects the form factor, cost, treatment speed and overall attractiveness of a photoepilation-based device (particularly where the light energy is generated using light emitting diodes (LEDs)).

Currently available devices require the user to position the device over an area of skin, trigger an energy pulse, manually move the device to another area of skin (e.g. a neighbouring area), trigger an energy pulse, and so on, until the user considers that the part of the body has been adequately treated. As a result of this, users of photoepilation devices face difficulties in efficiently and effectively using these devices over large areas of skin, for example the legs. The difficulties arise from the combination of a relatively large area of skin to be treated, a small device treatment window area, a lack of information on areas that have already been treated, inaccuracy in repositioning the device over a non-treated area with or without a sufficient overlap with a previously treated area (for example a slight overlap may be desirable for effective treatment using some types of photoepilation devices), and inherent limited patience of the user in ensuring full treatment coverage.

These user-dependent issues result in high variability in compliance, treatment time and ultimately, treatment efficacy. In fact, based on an internal study, the measured treatment time of lower legs of 104 subjects varies from a minimum of 2:50 (minutes:seconds) to a maximum of 34:46 with a mean value of 13:49, with the recommended time of treatment for the lower leg being 8 minutes.

US 2014/0005756 A1 discloses a self-contained, handheld device for providing a dermatological treatment including a device body configured to be handheld by a user, a radiation source including a beam source configured to generate an energy beam, an application end configured to be manually moved across the surface of the skin, a sensor configured to generate signals based on an interaction with the skin, and electronics configured to automatically identify a series of intrinsic skin features based on the sensor signals, and control at least one operational parameter of the radiation source based at least on the identification of such skin features.

SUMMARY OF THE INVENTION

It is an objective to provide devices for performing treatment operations on skin using energy pulses that can enable a user to complete the treatment operation in a more efficient and effective manner. For example, rather than having to reposition the device and then manually trigger an energy pulse, it is an objective to enable energy pulses to be delivered or applied to the skin while the device is moving over the skin, for example similar to the motion a user may perform when using an electric or razor-based shaving device.

To enable this type of use, the delivery of the energy pulses should be carefully managed, since delivering multiple energy pulses to a particular area of skin may cause pain or long-term damage (e.g. burns). With the electrical-optical efficiencies of current light elements (e.g. flash lamps and LED arrays) that can be used in these types of devices, it is unlikely that it will be possible to treat a large area of skin (e.g. a leg) with full treatment coverage in a single pass while moving a device at a high stroke speed (e.g. a speed similar to when the skin is being shaved). It is therefore an objective to improve treatment coverage when a device is moved over skin in multiple passes (i.e. when moving the device up and down a leg), while reducing user difficulty in performing the treatment and reducing the risk of over treating a particular area of skin.

According to a first specific aspect, there is provided a handheld device for applying energy pulses to skin of a subject to perform a treatment operation as the handheld device is moved across the skin, the handheld device comprising an aperture that is to be placed adjacent to the skin; at least one energy source for generating an energy pulse and for providing the energy pulse through the aperture to perform the treatment operation on skin adjacent the aperture, wherein the at least one energy source has a minimum pulse repetition period following the generation of an energy pulse before a subsequent energy pulse can be generated; a first skin property sensor for measuring a skin property and for outputting a first measurement signal representing measurements of the skin property at a first sensing position, wherein the skin property is a property that changes in response to the application of an energy pulse to the skin, and wherein the first sensing position is in front of the aperture relative to an intended motion direction of the handheld device over the skin; a second skin property sensor for measuring the skin property and for outputting a second measurement signal representing measurements of the skin property at a second sensing position, wherein the second sensing position is behind the aperture relative to the intended motion direction; a memory unit; and a control unit that is coupled to the at least one energy source to control the generation of energy pulses by the at least one energy source, and coupled to the first skin property sensor and the second skin property sensor to obtain the first measurement signal and the second measurement signal. The control unit is configured to store a profile of at least the first measurement signal in the memory unit. The control unit is further configured to, when the handheld device is moving in the intended motion direction over the skin, analyse the profile of the first measurement signal to determine if the first skin property sensor is passing over a previously treated area of skin; on detecting that the first skin property sensor is not passing over a previously treated area of skin, control the at least one energy source to generate an energy pulse if, or once, the minimum pulse repetition period following the generation of a previous energy pulse has expired; on detecting that the first skin property sensor is passing over a previously treated area of skin, perform the consecutive operations of: preventing the generation of an energy pulse, even if the minimum pulse repetition period following the generation of a previous energy pulse has expired; marking a point in the profile of the first measurement signal stored in the memory unit according to a predetermined rule, wherein the marked point relates to a position on the previously treated area of skin; using information about the marked point, analyse the profile of the second measurement signal to identify a similar marked point in the profile of the second measurement signal; on identifying the similar marked point in the profile of the second measurement signal, controlling the at least one energy source to generate an energy pulse if, or once, the minimum pulse repetition period following the generation of a previous energy pulse has expired.

According to a second aspect, there is provided a computer program product comprising a computer readable medium having computer readable code embodied therein, the computer readable code being configured for execution by a control unit in a handheld device. The handheld device comprises an aperture that is to be placed adjacent to the skin; at least one energy source for generating an energy pulse and for providing the energy pulse through the aperture to perform the treatment operation on skin adjacent the aperture, wherein the at least one energy source has a minimum pulse repetition period following the generation of an energy pulse before a subsequent energy pulse can be generated; a first skin property sensor for measuring a skin property and for outputting a first measurement signal representing measurements of the skin property at a first sensing position, wherein the skin property is a property that changes in response to the application of an energy pulse to the skin, and wherein the first sensing position is in front of the aperture relative to an intended motion direction of the handheld device over the skin; a second skin property sensor for measuring the skin property and for outputting a second measurement signal representing measurements of the skin property at a second sensing position, wherein the second sensing position is behind the aperture relative to the intended motion direction; and a memory unit; the control unit is coupled to the at least one energy source to control the generation of energy pulses by the at least one energy source, and coupled to the first skin property sensor and the second skin property sensor to obtain the first measurement signal and the second measurement signal, wherein the control unit is configured to store a profile of at least the first measurement signal in the memory unit. On execution of the computer readable code by the control unit, the control unit is caused to, when the handheld device is moving in the intended motion direction over the skin: analyse the profile of the first measurement signal to determine if the first skin property sensor is passing over a previously treated area of skin; on detecting that the first skin property sensor is not passing over a previously treated area of skin, control the at least one energy source to generate an energy pulse if, or once, the minimum pulse repetition period following the generation of a previous energy pulse has expired; on detecting that the first skin property sensor is passing over a previously treated area of skin, perform the consecutive operations of: preventing the generation of an energy pulse, even if the minimum pulse repetition period following the generation of a previous energy pulse has expired; marking a point in the profile of the first measurement signal stored in the memory unit according to a predetermined rule, wherein the marked point relates to a position on the previously treated area of skin; using information about the marked point, analyse the profile of the second measurement signal to identify a similar marked point in the profile of the second measurement signal; on identifying the similar marked point in the profile of the second measurement signal, controlling the at least one energy source to generate an energy pulse if, or once, the minimum pulse repetition period following the generation of a previous energy pulse has expired.

These and other aspects will be apparent from and elucidated with reference to the embodiment(s) described hereinafter.

BRIEF DESCRIPTION OF THE DRAWINGS

Exemplary embodiments will now be described, by way of example only, with reference to the following drawings, in which:

FIG. 7 is a pair of plots showing exemplary sensor measurement signals and the processing thereof;

FIG. 8 is a flow chart illustrating the operation of a handheld device to apply energy pulses to skin of a subject to perform a treatment operation;

DETAILED DESCRIPTION OF EMBODIMENTS

Figure 1:
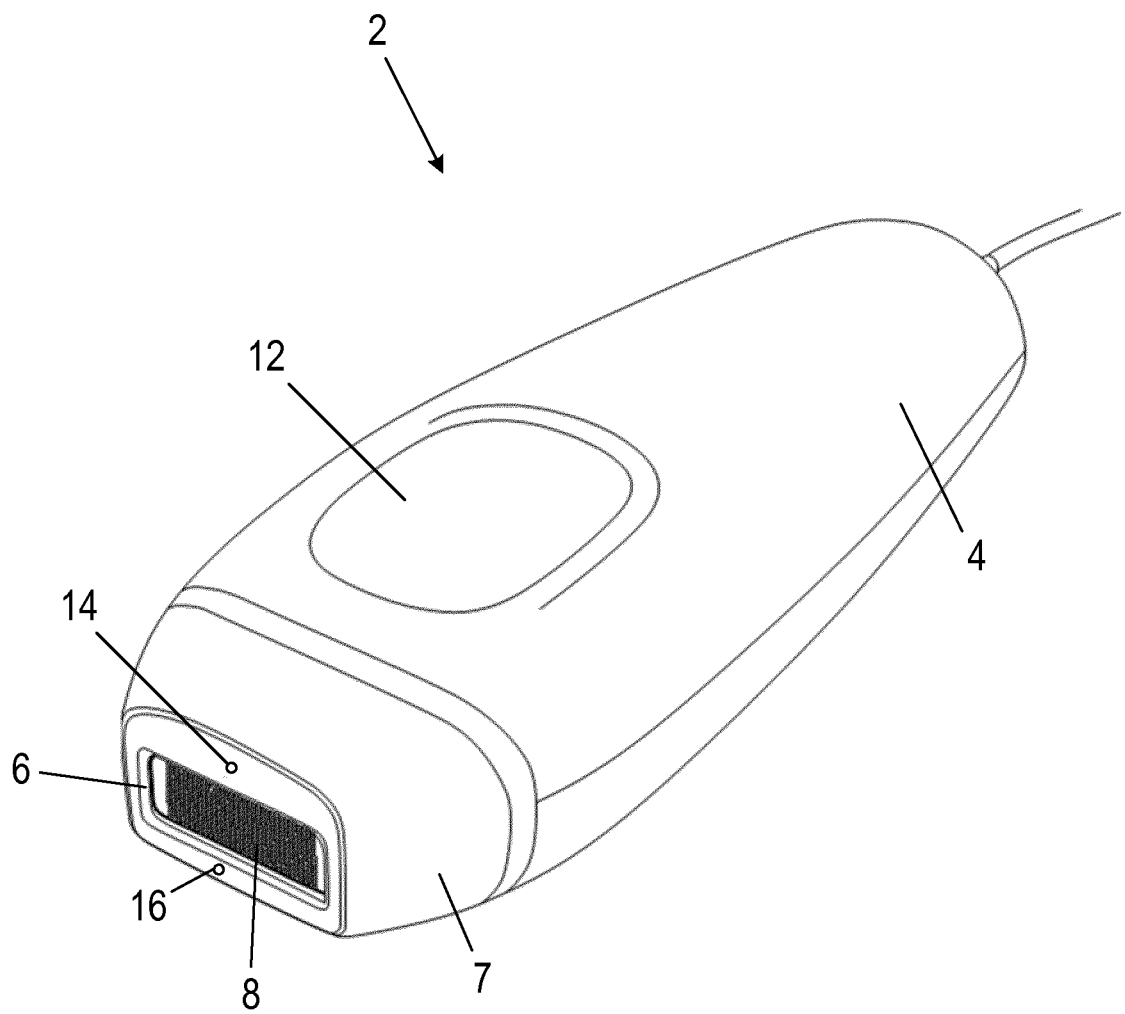
FIG. 1 is an illustration of a handheld device according to an embodiment.
Figure 2:
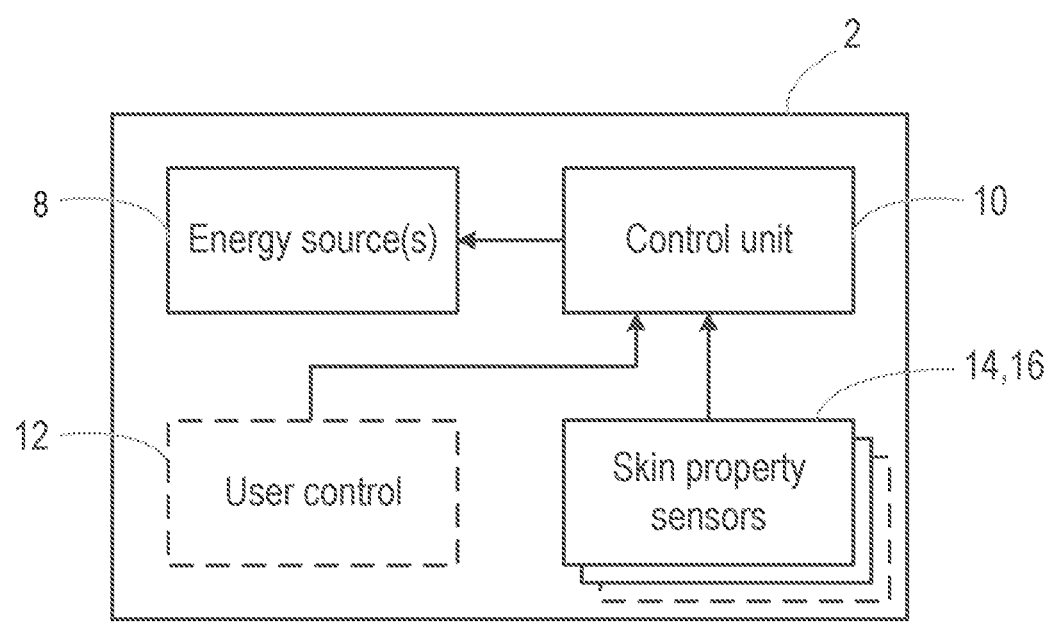
FIG. 2 is a block diagram illustrating exemplary components of a handheld device according to an embodiment.

FIG. 1 is an illustration of a handheld device 2 according to various embodiments, and FIG. 2 is a block diagram of the handheld device 2 of FIG. 1. The handheld device 2 is for performing a treatment operation on the skin of a subject using energy pulses. As described herein, the handheld device 2 is operated or used by a 'user', and the treatment operation is performed on a 'subject'. In some cases the user and the subject is the same person, i.e. the handheld device 2 is held in a hand and used by a user on themselves (e.g. for treating the skin on their leg). In other cases the user and the subject are different people, e.g. the handheld device 2 is held in a hand and used by a user on someone else. The treatment operation can be any type of treatment operation that is typically performed using energy pulses, such as light pulses. For example, the treatment operation can be hair removal, hair reduction, photoepilation, phototherapy treatment, skin rejuvenation, skin tightening, port-wine stain treatment, or pain relief.

The handheld device 2 comprises a body or housing 4 that includes an aperture 6 at one end 7 of the body 4 (referred to herein as the 'treatment end' 7). The aperture 6 is arranged in or on the body 4 so that the aperture 6 can be placed adjacent to or on (i.e. in contact with) the skin of the subject. The handheld device 2 includes one or more energy sources 8 that are for generating energy pulses that are to be applied to the skin of the subject via the aperture 6 and effect a treatment operation. The one or more energy sources 8 are arranged in the body 4 so that the energy pulses are provided from the one or more energy sources 8 through the aperture 6. The aperture 6 may be in the form of an opening at one end of the body 4, or it may be in the form of a window (including a waveguide) that is transparent or semi-transparent to the energy pulses (i.e. the energy pulses can pass through the window).

The part of the skin of the subject that is 'visible' to the one or more energy sources 8 through the aperture 6 when the aperture 6 is placed adjacent to or on the skin of the subject is referred to herein as the "current skin treatment region". The part of the skin of the subject that corresponds to the "current skin treatment region" will therefore change as the handheld device 2 is moved across the skin of the subject.

In the exemplary embodiment shown in FIG. 1, the aperture 6 has a generally rectangular shape, which results in a generally rectangular-shaped skin treatment region on the skin. It will be appreciated that the aperture 6 can have any other desired shape. For example the aperture 6 can be square, elliptical, circular, or any other polygonal shape.

The one or more energy sources 8 can generate any suitable type of energy for performing a treatment operation, for example light, sound, radio frequency (RF) signals, microwave radiation and plasma. In the case of an energy source 8 that generates light, the energy source 8 can be configured to generate a light pulse at any suitable or desired wavelength (or range of wavelengths) and/or intensities. For example, the energy source 8 can generate visible light, infra-red (IR) light and/or ultraviolet (UV) light. Each energy source 8 can comprise any suitable type of light source, such as one or more light emitting diodes (LEDs), a (Xenon) flash lamp, a laser or lasers, etc. In a preferred embodiment, the handheld device 2 is for performing photoepilation, and the energy source(s) 8 are to provide intense light pulses. In the case of an energy source 8 that generates sound, the energy source 8 can be configured to generate a sound pulse at any suitable or desired wavelength (or range of wavelengths) and/or intensities. For example, the energy source 8 can be an ultrasound transducer.

The one or more energy sources 8 is configured to provide pulses of energy. That is, the energy source(s) 8 are configured to generate energy at a high intensity for a short duration (e.g. less than 1 second). The intensity of the energy pulse should be high enough to effect the treatment operation on the skin in the current skin treatment region.

Although not shown in FIG. 1, the energy source(s) 8 can include suitable driving circuitry or components for causing the energy source(s) 8 to generate the energy pulses in response to a trigger signal.

Where the one or more energy sources 8 comprises a plurality of energy sources 8, the plurality of energy sources 8 may comprise two or more types of energy sources 8, for example for performing different types of treatment operation. Alternatively, the plurality of energy sources 8 may comprise energy sources 8 of the same type, but the energy sources 8 may be spatially separated so that they apply energy pulses to respective parts of the skin in the current skin treatment region.

In addition, where the one or more energy sources 8 comprises a plurality of energy sources 8, the energy sources 8 may be separately controllable, so that, for example, any one or more of the energy source(s) 8 can be activated at any particular time. This individual control of the activation of the energy sources 8 is described in more detail below.

The one or more energy sources 8 have a so-called "minimum pulse repetition period" following the generation of an energy pulse before a subsequent energy pulse can be generated. This minimum pulse repetition period can be due to the time required to 'charge up' the driving circuitry for the one or more energy sources 8 (e.g. charging a capacitor) before an energy pulse can be generated and/or the time required for the one or more energy sources 8 to cool down following the generation of an energy pulse (for example where generating the energy pulse, or the energy pulse itself, has the effect of heating the energy source(s) 8 and/or other components of the handheld device 2). A typical repetition rate for energy pulses due to some or all of the above factors is between 0.33 Hz and 1 Hz (corresponding to minimum pulse repetition periods of between 1 second and 3 seconds). Typically, the minimum pulse repetition period of the energy source(s) 8 is longer than a so-called "dwell time", which is the time that the aperture 6 takes to move completely over a point on the skin when the handheld device 2 is being moved by the user over the skin at typical usage speeds.

In FIG. 2, the handheld device 2 comprises the one or more energy sources 8 and a control unit 10 that is for controlling the operation of the handheld device 2, including controlling the operation of the energy source(s) 8 to generate energy pulses to perform a treatment operation according to the techniques described herein. The control unit 10 is electrically coupled to the one or more energy sources 8 so that the control unit 10 can trigger the energy source(s) 8 to generate energy pulses.

The handheld device 2 shown in FIGS. 1 and 2 includes a user control 12 that can be operated by the user to activate the handheld device 2 and lead to the generation of an energy pulse by the one or more energy source(s) 8 (subject to the re-charge period from the last energy pulse having passed) under the control of the control unit 10. The user control 12 may be such that the user actuates the user control 12 while the handheld device 2 is in contact with the skin and being moved across the skin by the user, and the control unit 10 is able to trigger the energy source(s) 8 to generate energy pulses in accordance with the techniques described below. The user control 12 may be in the form of a switch, a button, a touch pad, etc.

The handheld device 2 also includes at least two skin property sensors 14, 16 for measuring a skin property during operation of the handheld device 2. Each skin property sensor 14, 16 is positioned in the handheld device 2 so that it can measure the skin property at a respective sensing position on the skin of the subject. Each respective sensing position has a predefined spatial relationship with respect to the aperture 6 and thus a predefined spatial relationship with respect to the skin that forms the current skin treatment region (which is defined by the aperture 6). Typically, the size of the area of skin sensed by each skin property sensor 14, 16 at the respective sensing position is much smaller than the size of the current skin treatment region. The at least two skin property sensors 14, 16 are connected to the control unit 10 and provide measurements of the skin property to the control unit 10 for analysis and/or processing. In particular, the control unit 10 analyses the measurements of the skin property to determine if an energy pulse can be applied to the skin in the current skin treatment region.

In FIG. 1, a first skin property sensor 14 is positioned close to (but spaced from) the mid-point of a long edge of the generally rectangular aperture 6 and a second skin property sensor 16 is positioned close to (but spaced from) the mid-point of the opposite long edge of the rectangular aperture 6. The skin property sensors 14, 16 are positioned so that, during typical movement of the handheld device 2 over the skin (e.g. in a direction that is in the plane of the aperture 6 and perpendicular to the long edge of the aperture 6), one of the skin property sensors 14, 16 is 'in front' of the aperture 6 so that it measures the skin property of skin that is about to be covered by the aperture 6 (and is thus skin that is about to be part of the current skin treatment region), and the other one of the skin property sensors 14, 16 is 'behind' the aperture 6 so that it measures the skin property of skin that has just been covered by the aperture 6.

The at least two skin property sensors 14, 16 measure the same skin property at their respective sensing positions.

Figure 3:
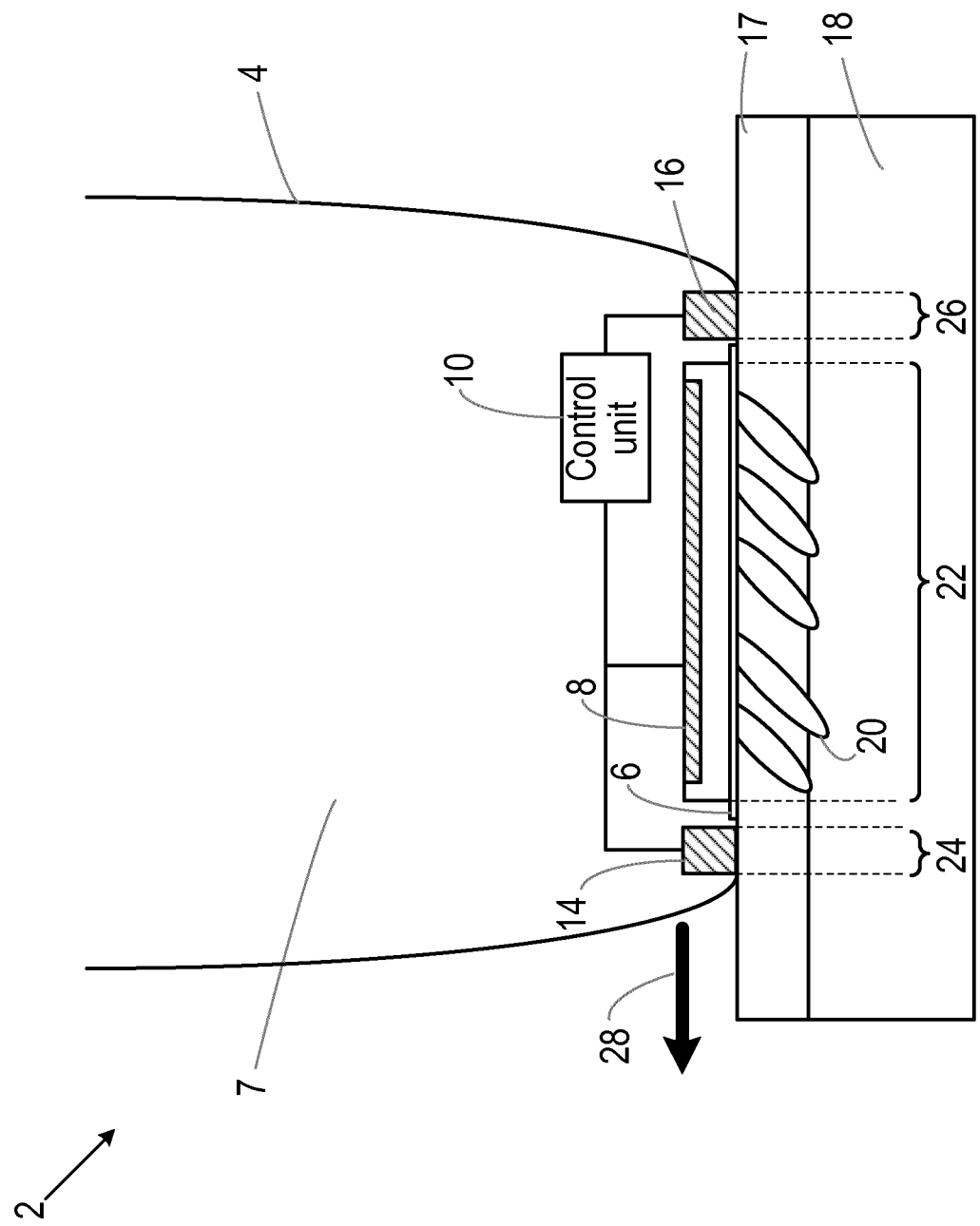
FIG. 3 is an illustration of the handheld device according to FIG. 1 adjacent to skin.

FIG. 3 shows the exemplary handheld device 2 of FIGS. 1 and 2 placed adjacent to the skin of a subject so that a treatment operation can be performed. Thus, the handheld device 2 is placed so that the aperture 6 (here in the form of a window) is in contact with the skin 17. Part of the bodily tissue 18 below the skin 17 is shown, along with several hairs/hair follicles 20. The energy source(s) 8 and the aperture 6 define the current skin treatment region 22 on the skin 17.

The sensing position 24 of the first skin property sensor 14 is shown, and it can be seen that the sensing position 24 is adjacent to the current skin treatment region 22. Likewise, the sensing position 26 of the second skin property sensor 16 is shown, and it can be seen that the sensing position 26 is also adjacent to the current skin treatment region 22. In the following explanation of the techniques described herein, it is assumed that the handheld device 2 is moved over the skin in the direction indicated by arrow 28 (i.e. a direction that is perpendicular to the long edge of the aperture 6 and in the plane of the aperture 6) which means that the first skin property sensor 14 is 'ahead of' the aperture 6 and the second skin property sensor 16 is behind the aperture 6. It will be appreciated that if the handheld device 2 is moved in the opposite direction, the roles of the first skin property sensor 14 and the second skin property sensor 16 are reversed (i.e. the second skin property sensor 16 is ahead of the aperture 6 and the first skin property sensor 14 is behind the aperture 6). In the following explanation, reference is made to a 'front' skin property sensor, which refers to whichever one of the first skin property sensor 14 and the second skin property sensor 16 is ahead of the aperture 6, and a 'back' skin property sensor, which refers to whichever one of the first skin property sensor 14 and the second skin property sensor 16 is behind the aperture 6.

In some embodiments, as the techniques described herein aim to provide a handheld device 2 that can be moved over the skin of a subject is any direction (e.g. up and down a leg), the handheld device 2 can further comprise a sensor that provides an indication of the direction of movement of the handheld device 2. For example, the handheld device 2 can include a movement sensor, such as an accelerometer, and the measurement signal from the movement sensor can be analysed by the control unit 10 to determine the direction in which the handheld device 2 is being moved.

The information on the direction in which the handheld device 2 is being moved can be used by the control unit 10 to determine which of the first skin property sensor 14 and the second skin property sensor 16 is the front skin property sensor and the second skin property sensor. In alternative embodiments, the control unit 10 can determine the direction of movement of the handheld device 2 by analysing the measurement signals from the skin property sensors 14, 16, and so a separate movement sensor is not required. For example, the control unit 10 can analyse the measurement signals to identify corresponding signal features in the measurement signals (e.g. a particular peak that occurs in both measurement signals), and determine which sensor is in front of the other based on the relative timing of the corresponding signal features. The measurement signal that is lagging behind the other (i.e. the measurement signal that has the signal feature occurring at a later time) is the measurement signal from the back skin property sensor 16.

It is not essential that the handheld device is configured to determine the direction of movement. Alternatively, a user of the device may be instructed in the user's manual to use the device only in one direction. Another alternative could be to construct the device such that it can be moved over the skin in only one direction, e.g. it has a wheel rolling over the skin that can turn in one rotation direction only. In these situations, the first and second skin property sensor are fixed, because the motion direction relative to the handheld device will not change.

As described in more detail below, measurements obtained by the skin property sensors 14, 16 are analysed by the control unit 10 to identify areas of skin that have already been recently (and/or sufficiently) treated by energy from the energy source(s) 8, and the control unit 10 controls the energy source(s) 8 so that energy pulses are applied to parts of the skin of the subject that have not recently (and/or sufficiently) been treated. This prevents or otherwise reduces the risk of over treating a part of the body of the subject with energy pulses, while maximising the treatment coverage area.

Thus, to enable this control of the energy source(s) 8, the skin property sensors 14, 16 measure a skin property that changes in response to the application of an energy pulse to the skin. In some embodiments, the skin property is a property of the skin that has a short-term (i.e. temporary) response to the application of an energy pulse to the skin. That is, the skin property responds to the application of the energy pulse, so the value of the property changes from an initial value as the energy pulse is applied or shortly after (e.g. within 1 or 2 seconds), and the value of the property returns to the initial value over a short period of time (e.g. within a few tens of seconds or minutes). Alternatively, the skin property could respond to the application of the energy pulse over a longer period of time, so the value of the property can change from an initial value after an energy pulse is applied (e.g. after a few minutes or hours), and the value of the property does not return to the initial value for some time (e.g. after a few days). Skin properties that change in the short term include temperature and blood perfusion, whereas a skin property that changes over a longer period includes hyperpigmentation.

In preferred embodiments, the skin property is skin temperature, particularly the surface temperature of the skin, as the application of an energy pulse or energy pulses to the skin may temporarily heat that part of the skin. Therefore, the skin property sensors 14, 16 can be skin temperature sensors. Each of the skin temperature sensors 14, 16 can be a contact temperature sensor (i.e. a sensor that requires contact with the skin to measure the temperature of the skin), such as a thermocouple, a thermistor or a resistance temperature detector (RTD). Alternatively each skin temperature sensor 14, 16 can be a non-contact temperature sensor (i.e. a sensor that does not require contact with the skin to measure the temperature of the skin), such as an infrared (IR) thermal sensor. This type of skin temperature sensor is also referred to as an optical thermal sensor. In an exemplary embodiment, each skin property sensor 14, 16 can be a thermopile infrared sensor (e.g. Thermopile sensor TS318-1B0814 produced by TE connectivity). This type of sensor, or similar non-contact skin temperature sensors, can be positioned close to the aperture 6 (e.g. as shown in FIGS. 1 and 2) with the sensors 14, 16 having an opening angle of 120 degrees.

In other embodiments, the skin property is an optical property of the skin, for example an optical property of the skin that changes in response to incident energy pulses. The optical property could be, e.g., scattering, reflectance, etc., and each skin property sensor 14, 16 can be an optical sensor that measures light reflected or scattered from the skin 17. In some embodiments, the skin property sensors 14, 16 can include a light source for emitting light into or onto the skin, with the skin property sensors 14, 16 measuring the reflection or scattering of that light. Those skilled in the art will be aware of various techniques that can be used to measure the optical properties of the skin, including, for example, hyperspectral imaging, polarisation imaging and speckle imaging.

In other embodiments, the skin property is an acoustic property of the skin, for example an acoustic property of the skin that changes in response to incident energy pulses. The acoustic property could be, e.g., acoustic impedance, speed of sound, etc., and each skin property sensor 14, 16 can be an acoustic sensor, for example an ultrasound sensor. In some embodiments, the skin property sensors 14, 16 can include a sound source for emitting sound into the skin, with the skin property sensors 14, 16 measuring the sound to determine the acoustic skin property.

In other embodiments, the skin property is an electrical property of the skin, for example an electrical property of the skin that changes in response to incident energy pulses. The electrical property could be, e.g., radio frequency (RF) impedance, capacitance, etc., and each skin property sensor 14, 16 can be an RF sensor, an impedance sensor or a capacitance sensor.

In some embodiments, the handheld device 2 also includes one or more sensors for detecting whether the handheld device 2, and specifically the treatment end 7 or the aperture 6, is in contact with the skin 17 of the subject. The energy pulses generated by the energy source(s) 8 can have a high intensity, and so they should only be triggered if the energy pulse will be directed into the skin and not, for example, into the subject's eyes. Therefore one or more skin contact sensors can be provided that is/are coupled to the control unit 10 and that enables the control unit 10 to determine if the treatment end 7 or aperture 6 is in contact with the skin. In the case of multiple skin contact sensors arranged around the aperture 6, in some embodiments all of the sensors can be required to detect skin contact at the same time in order for an energy pulse to be triggered. Each skin contact sensor may be in the form of a pressure sensor that is located close to the aperture 6. Alternatively, each skin contact sensor may be in the form of a conductivity sensor that is located close to the aperture 6 and that detects when skin is in contact with the treatment end 7 or aperture 6 via a change in the measured conductivity. Other types of skin contact sensor include capacitive contact sensors, proximity sensors and optical-based contact sensors (e.g. that can detect contact based on a measured light level). The skin contact sensor is not shown in FIG. 1, 2 or 3. It will be appreciated that in some embodiments, the skin property sensors 14, 16 can also be used as a skin contact sensor (or put another way, the measurement signal from one or both of the skin property sensors 14, 16 can be analysed or processed to determine if the treatment end 7 or aperture 6 is in contact with the skin. For example, the measurements from a skin temperature sensor can be processed to determine if the sensor is in contact with skin, since skin will typically have a higher temperature than the environment (i.e. air).

As noted above, the skin property sensor 14, 16 are provided to enable the control unit 10 to identify areas of skin that have been recently and/or sufficiently treated with energy pulses and to control the energy source(s) 8 to generate energy pulses when the handheld device 2 is at appropriate positions on the skin 17 of the subject. As part of this control, it is desirable for the control unit 10 to trigger energy pulses so that all of the relevant part of the body of the subject (e.g. a leg) is adequately treated with energy pulses, with no gaps or spaces, or only very small gaps or spaces, between each region of skin that has been treated with energy pulses. In addition, as energy pulses may not uniformly treat the skin in the skin treatment region, for example the intensity of the energy from the energy source(s) may be higher in the centre of the aperture 6 than in the periphery (e.g. in the corners and at the edges), it may be desirable for subsequent energy pulses to be applied in a skin treatment region that partially overlaps with a previous skin treatment region. Therefore, as the sensing positions 24, 26 of the skin property sensors 14, 16 are outside of the current skin treatment region 22 (for example so that the skin property sensors 14, 16 are not damaged by the energy pulses), the distance between the aperture 6 and the skin property sensor 14, 16 that is behind the aperture 6 should be known the control unit 10 so that the control unit 10 can determine from the measurements of the skin property whether the skin in the current skin treatment region 24 can be treated with an energy pulse.

Figure 4:
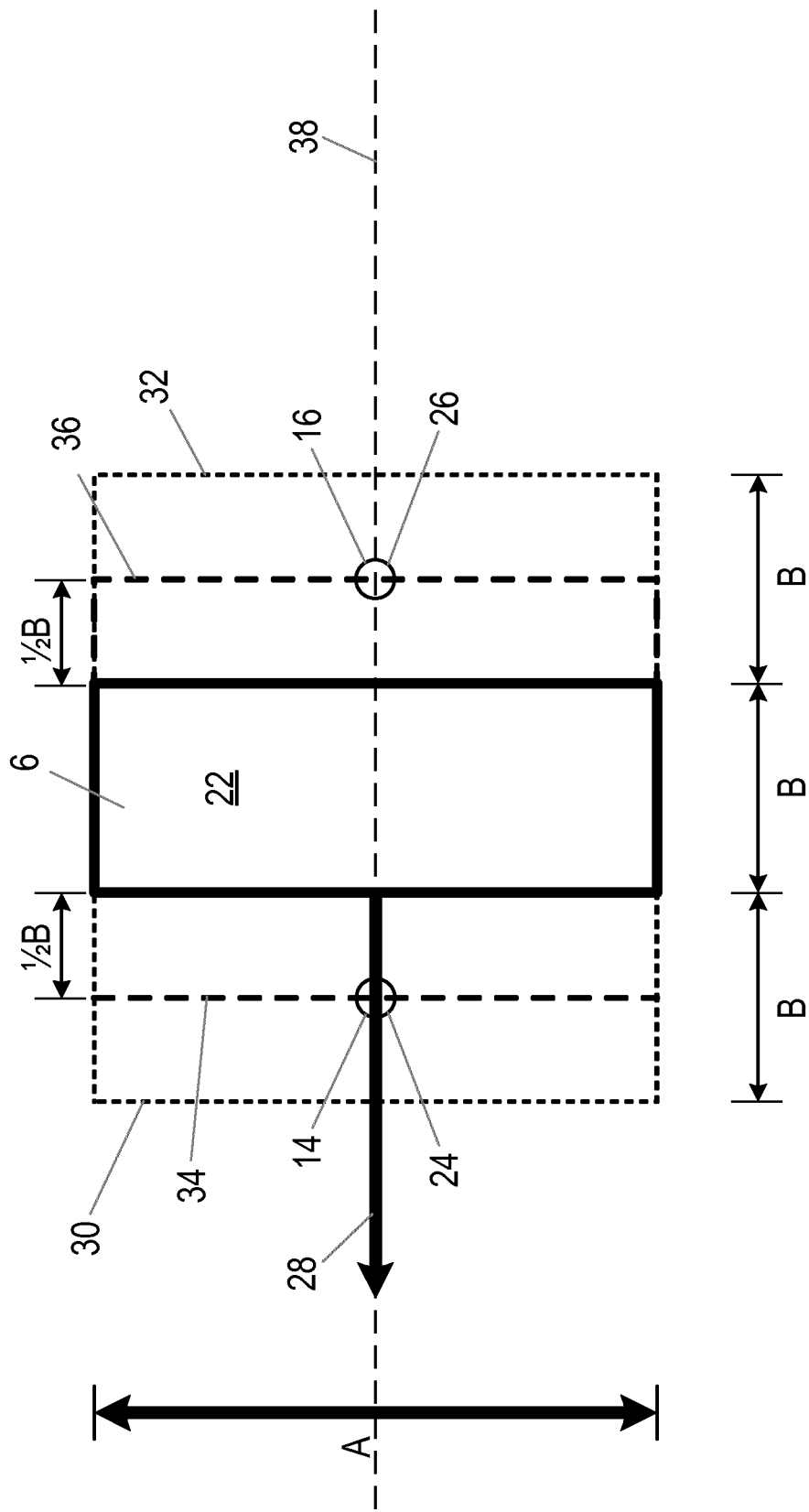
FIG. 4 is an illustration of an exemplary spatial relationship between a sensing position of a skin property sensor and a current skin treatment region.

FIG. 4 illustrates an exemplary spatial relationship between the skin property sensors 14, 16 and a current skin treatment region 22 defined by aperture 6. FIG. 4 is a view from the skin towards the treatment end 7 of handheld device 2, which shows the aperture 6 and corresponding current skin treatment region 22. In this example the aperture 6 and thus the current skin treatment region 22 are in a generally rectangular shape and have the same size (as the aperture 6 is in contact or adjacent to the skin), with a length A (measured along the long side) and a width B (measured along the short side). FIG. 4 illustrates the positioning of both of the first skin property sensor 14 and the second skin property sensor 16 with respect to the aperture 6. As noted further below, such positioning is desirable for a handheld device 2 that is to be able to apply energy pulses when the handheld device 2 is moved in a reciprocating motion (e.g.

up and down a leg). In the case of a handheld device 2 that is only to apply energy pulses when the handheld device 2 is moved in a single direction, the desirable positions of the skin property sensors 14, 16 apply only to the skin property sensor 14, 16 that is to be positioned behind the aperture 6 with respect to the intended motion direction.

The spatial relationships between the sensing position 24 of the first skin property sensor 14 and the current skin treatment region 22 and the sensing position 26 of the second skin property sensor 16 and the current skin treatment region 22 are such that the sensing position 24 and sensing position 26 are displaced from respective long edges of the current skin treatment region 22 (i.e. the edge that has length A) by no more than the width B of the current skin treatment region 22 (where the width is the dimension of the current skin treatment region 22 measured in the direction of movement of the handheld device 2 indicated by arrow 28 and the long edge of the current skin treatment region 22 is perpendicular to this direction). More generally, the sensing positions 24, 26 can be anywhere within an area substantially equal in size to the current skin treatment region 22, with the centre of the area being offset from the centre of the current skin treatment region 22 by a distance equal to the width B along the intended direction of movement (also referred to herein as "intended motion direction") of the handheld device 2 (as indicated by arrow 28). These areas are indicated by dotted boxes 30 and 32 in FIG. 4, with dotted box 30 being ahead of the current skin treatment region 22 when the handheld device 2 is moved in the direction indicated by arrow 28 (so the first skin property sensor 14 measures the skin property for skin that is about to pass through the current skin treatment region 22), and dotted box 32 being behind the current skin treatment region 22 when the handheld device 2 is moved in the direction indicated by arrow 28 (so the second skin property sensor 16 measures the skin property for skin that has just passed through the current skin treatment region 22). Put another way dotted boxes 30 and 32 define rectangular areas that are centred a distance that is half the width B from either edge of the current skin treatment region 22, with the areas 30, 32 having length A (i.e. the same as the current skin treatment region 22) and width B.

In some embodiments, the skin property sensors 14, 16 are spaced the same distance from the aperture 6, but in other embodiments they can be spaced different distances from the aperture 6.

In a more preferred implementation, the spatial relationships between the sensing positions 24, 26 and the current skin treatment region 22 may be such that the sensing positions 24, 26 are displaced from the long edges of the current skin treatment region 22 (i.e. the edges that have length A) by no more than half the width B of the current skin treatment region 22. More generally, the sensing positions 24, 26 can be anywhere within an area substantially equal to half the size of the current skin treatment region 22, with the area being adjacent to the current skin treatment region 22 and having a width (measured in the direction of movement indicated by arrow 26) that is half the width B of the current skin treatment region 22. This area is indicated by dashed boxes 34 and 36 in FIG. 4, with dashed box 34 being ahead of the current skin treatment region 22 when the handheld device 2 is moved in the direction indicated by arrow 28 (so the first skin property sensor 14 measures the skin property for skin that is about to pass through the current skin treatment region 22) and with dashed box 36 being behind the current skin treatment region 22 when the handheld device 2 is moved in the direction indicated by arrow 28 (so the second skin property sensor 16 measures the skin property for skin that has just passed through the current skin treatment region 22).

FIG. 4 shows an exemplary positioning of the sensing position 24 (and thus the first skin property sensor 14) in the middle of dotted box 30 and on the edge of dashed box 34 and an exemplary positioning of the sensing position 26 (and thus the second skin property sensor 16) in the middle of dotted box 32 and on the edge of dashed box 36.

It will be appreciated that where a single skin property sensor is provided on each side of the current skin treatment region 22 (i.e. as opposed to multiple skin property sensors on each side), the first skin property sensor 14 and second skin property sensor 16 are typically positioned in line with a mid-point of the length of the current skin treatment region 22 (where the length is measured in a direction that is perpendicular to the intended motion direction of the handheld device 2). For example, as shown in FIG. 4, the sensing positions 24, 26 are located on dashed line 38 that passes through the middle of the current skin treatment region 22 in the direction of movement shown by arrow 28.

Figure 5:
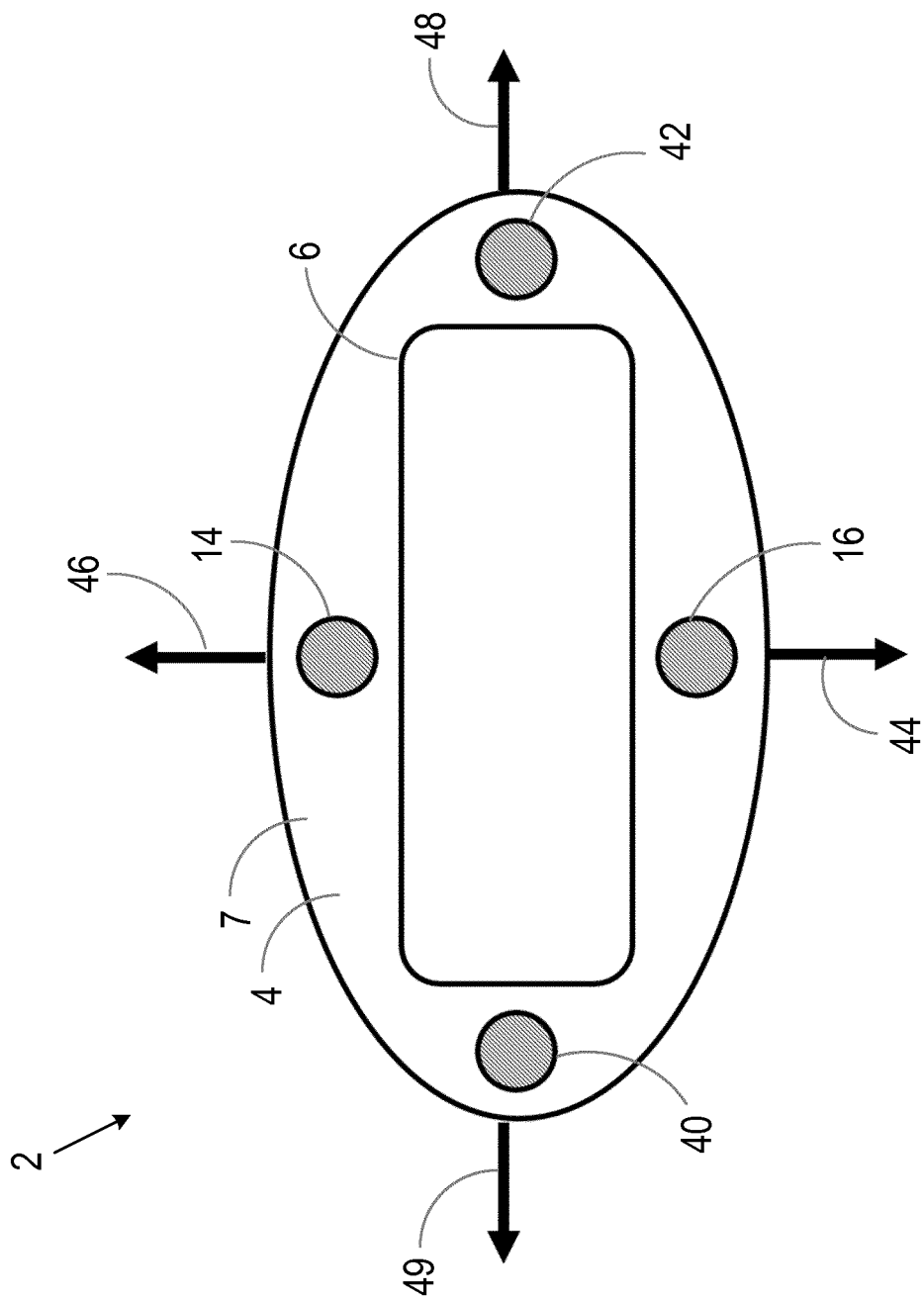
FIG. 5 is an illustration of a treatment end of a handheld device according to another exemplary embodiment.

In some embodiments, to enable a user of the handheld device 2 to move the handheld device 2 in any direction and for the triggering of the energy pulses to be controlled appropriately, the handheld device 2 includes at least four skin property sensors arranged on respective sides of the generally rectangular aperture 6. This is illustrated in FIG. 5. FIG. 5 shows the treatment end 7 of another exemplary handheld device 2 that includes four skin property sensors 14, 16, 40, 42. The first skin property sensor 14 and second skin property sensor 16 are positioned adjacent to the long sides of the generally rectangular aperture 6 as in FIGS. 1, 3 and 4. A third skin property sensor 40 is positioned adjacent to one of the short sides of the generally rectangular aperture 6, and a fourth skin property sensor 42 is positioned adjacent to the opposite short side of the generally rectangular aperture 6.

In the embodiment of FIG. 5, if the handheld device 2 is moved over the skin in a direction indicated by arrow 44 (i.e. a direction that is perpendicular to the long edge of the aperture 6 and in the plane of the aperture 6), then the first skin property sensor 14 measures the skin property of skin that has just been in the current skin treatment region, and the second skin property sensor 16 measures the skin property of skin that is about to be in the current skin treatment region. If the handheld device 2 is moved over the skin in the opposite direction, i.e. as indicated by arrow 46 (which is the same direction as arrow 28 in FIGS. 3 and 4), then the second skin property sensor 16 measures the skin property of skin that has just been in the current skin treatment region, and the first skin property sensor 14 measures the skin property of skin that is about to be in the current skin treatment region. If the handheld device 2 is moved over the skin in a direction indicated by arrow 48 (i.e. a direction that is perpendicular to the short edge of the aperture 6 and in the plane of the aperture 6), then the third skin property sensor 40 measures the skin property of skin that has just been in the current skin treatment region, and the fourth skin property sensor 42 measures the skin property of skin that is about to be in the current skin treatment region. If the handheld device 2 is moved over the skin in the opposite direction, i.e. as indicated by arrow 49, then the fourth skin property sensor 42 measures the skin property of skin that has just been in the current skin treatment region, and the third skin property sensor 40 measures the skin property of skin that is about to be in the current skin treatment region. Thus, the embodiment in FIG. 5 allows the user to move the handheld device 2 over the skin in any of the four different directions shown by arrows 44, 46, 48 and 49 and obtain the required measurements of the skin property for skin before and after passing through the current skin treatment region 22.

The third and fourth skin property sensors 40, 42 in FIG. 5 can be arranged so the respective sensing positions have a spatial relationship with respect to the current skin treatment region 22 according to the principles set out in relation to FIG. 4. The third and fourth skin property sensors 40, 42 can be positioned such that the respective sensing positions are displaced from respective short edges of the current skin treatment region 22 (i.e. the edge that has length B) by no more than the length A of the current skin treatment region 22 (where the width is the dimension of the short edge of the current skin treatment region 22 measured in the direction of movement of the handheld device 2 indicated by arrow 28 and the long edge of the current skin treatment region 22 is perpendicular to this direction). More generally, the sensing position 24 for the third and fourth skin property sensors 40, 42 can be anywhere within an area substantially equal in size to the current skin treatment region 22, with the centre of the area being offset from the centre of the current skin treatment region 22 by a distance equal to the length A perpendicular to the intended direction of movement of the handheld device 2 (as indicated by arrow 28).

Similar to FIG. 4, in a more preferred implementation, the spatial relationship between the respective sensing positions for the third and fourth skin property sensors 40, 42 and the current skin treatment region 22 may be such that the respective sensing positions are displaced from the short edge of the current skin treatment region 22 (i.e. the edge that has length B) by no more than half the width A of the current skin treatment region 22. More generally, the sensing positions can be anywhere within an area substantially equal to half the size of the current skin treatment region 22, with the area being adjacent to the current skin treatment region 22 and having a length (measured perpendicularly to the direction of movement indicated by arrow 28) that is half the length A of the current skin treatment region 22.

It will be appreciated that the specific spatial position of the sensing positions of the skin property sensors 14 with respect to the current skin treatment region 22 can be selected based on whether any overlap in treated areas of skin is desired or permitted. For example, depending on the processing of the skin property measurements by the control unit 10, arranging the skin property sensors so that the sensing positions are closer to the current skin treatment region 22 will increase the likelihood that the current skin treatment region 22 could include part of a region of skin that an energy pulse has previously been applied to.

As noted above, the control unit 10 controls the operation of the handheld device 2, and specifically the application of energy pulses to the skin 17 of the subject based on the skin property measurements according to the techniques described herein. The control unit 10 can be implemented in numerous ways, with software and/or hardware, to perform the various functions described herein. The control unit 10 may comprise one or more microprocessors or digital signal processor (DSPs) that may be programmed using software or computer program code to perform the required functions and/or to control components of the control unit 10 to effect the required functions. The control unit 10 may be implemented as a combination of dedicated hardware to perform some functions (e.g. amplifiers, pre-amplifiers, analog-to-digital convertors (ADCs) and/or digital-to-analog convertors (DACs)) and a processor (e.g., one or more programmed microprocessors, controllers, microcontrollers, DSPs and associated circuitry) to perform other functions. Examples of components that may be employed in various embodiments of the present disclosure include, but are not limited to, conventional microprocessors, DSPs, application specific integrated circuits (ASICs), and field-programmable gate arrays (FPGAs).

The control unit 10 can be connected to or comprise a memory unit (not shown in FIG. 2 or 3) that can store data, information and/or signals for use by the control unit 10 in controlling the operation of the handheld device 2 and/or in executing or performing the operations described herein. In some implementations the memory unit stores computer-readable code that can be executed by the control unit 10 so that the control unit 10 performs one or more functions, including the operations described herein. The memory unit can comprise any type of non-transitory machine-readable medium, such as cache or system memory including volatile and non-volatile computer memory such as random access memory (RAM) static RAM (SRAM), dynamic RAM (DRAM), read-only memory (ROM), programmable ROM (PROM), erasable PROM (EPROM) and electrically erasable PROM (EEPROM), implemented in the form of a memory chip, an optical disk (such as a compact disc (CD), a digital versatile disc (DVD) or a Blu-Ray disc), a hard disk, a tape storage solution, or a solid state device, including a memory stick, a solid state drive (SSD), a memory card, etc.

It will be appreciated that a practical implementation of handheld device 2 may include additional components to those shown in FIGS. 1-5. For example the handheld device 2 may also include a power supply, such as a battery, or components for enabling the handheld device 2 to be connected to a mains power supply. As another example, the handheld device 2 may include or use a manual triggering mode (that the user can select as an alternative to the automatic triggering of the energy pulses by the control unit 10 based on the skin property measurements), in which the control unit 10 determines when an energy pulse can be triggered based on the skin property measurements, and provides an indication to the user of when an energy pulse can be triggered. The indication can be provided in the form of a visual indication (e.g. a light using a light source or visual message on a display screen located in the body 4 of the handheld device 2 and visible to the user during use), an audible indication (e.g. a sound, such as a beep, using a sound source, e.g. a loudspeaker) or a tactile indication (e.g. a vibration generated using a vibrating element located inside the body 4).

Figure 6:
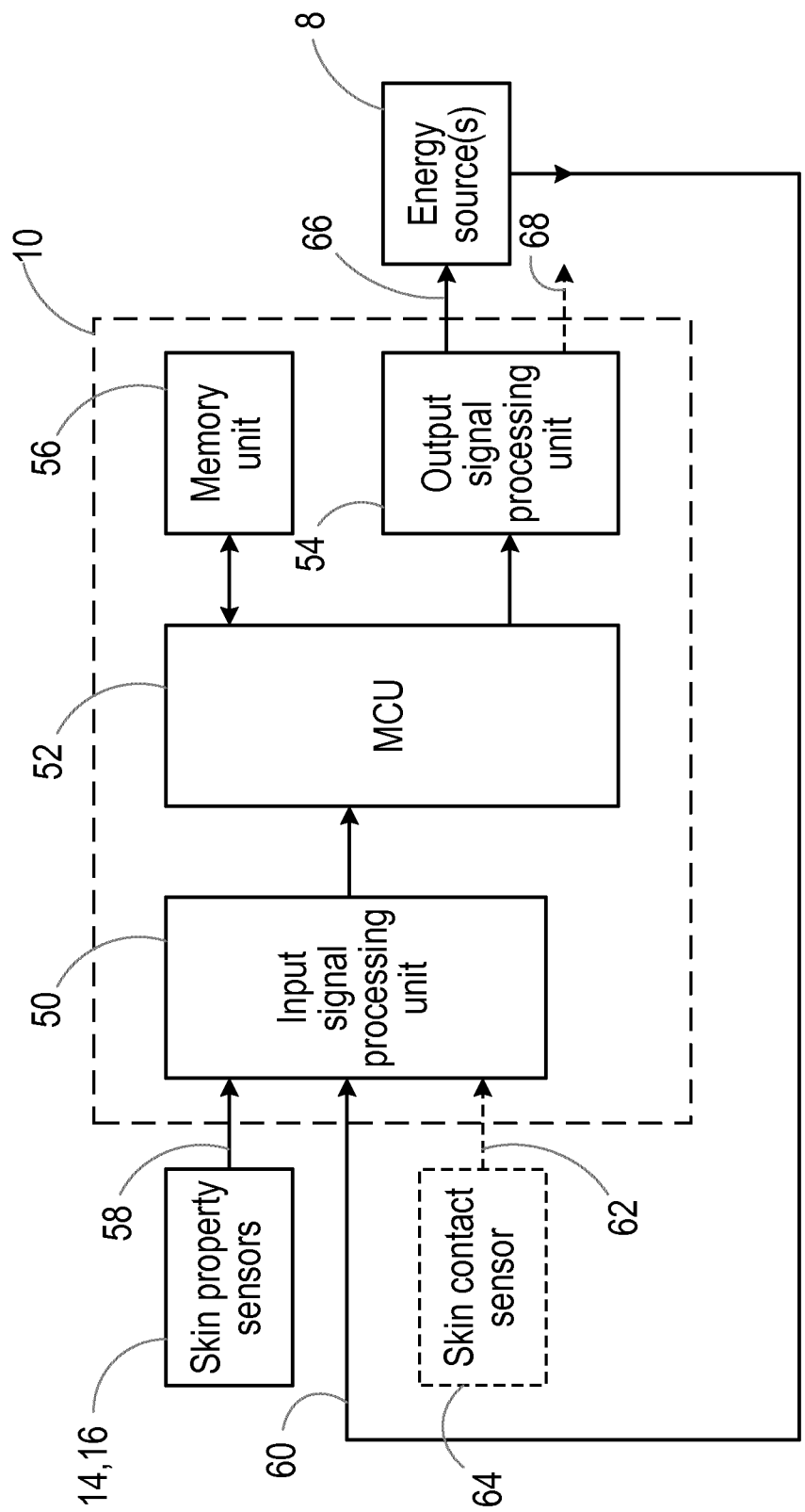
FIG. 6 is a block diagram of a control unit according to various embodiments.

An exemplary implementation of a control unit 10 in a handheld device 2 according to various embodiments is shown in FIG. 6. In this exemplary implementation, the control unit 10 comprises an input signal processing unit 50, a microcontroller unit (MCU) 52, an output signal processing unit 54 and a memory unit 56. The microcontroller unit 52 is connected or coupled to each of the input signal processing unit 50, the output signal processing unit 54 and the memory unit 56. The input signal processing unit 50 receives input signals in the form of voltage signals, performs analog-to-digital conversion of the voltage signals and sends the digitised signals to the MCU 52. In particular the input signal processing unit 50 can receive respective skin property measurement signals 58 from skin property sensors 14, 16 (and any other skin property sensors present in the handheld device 2) and may receive a signal 60 from the energy source(s) 8 indicating whether the energy source(s) 8 are ready to generate an energy pulse (i.e. a signal indicating whether the minimum pulse repetition period has expired following a previous energy pulse or from activation of the handheld device 2). The signal 60 is also referred to herein as a 'pulse ready signal 60'. The pulse ready signal 60 can be a high/low voltage signal indicating whether the energy source(s) 8 are currently able to generate an energy pulse. As an alternative to receiving the pulse ready signal 60, the 'pulse ready' state can be determined by the MCU 52 based on the time that has elapsed since the last pulse. If information about whether the treatment end 7 or aperture 6 is in contact with skin is required, the input signal processing unit 50 can also receive a skin contact signal 62 from a skin contact sensor 64 indicating whether the treatment end 7 or aperture 6 of the handheld device 2 is in contact with skin. Alternatively, this information can be derived from the skin property measurement signal(s) 58 by the MCU 52, in which case skin contact sensor 64 is not required. Each of the signals 58, 60 and 62 can be digitised by the input signal processing unit 50 and provided to the MCU 52.

Each skin property measurement signal 58 can be a signal whose voltage is proportional to the measured value of the skin property in the respective sensing position of the skin property sensor. For example the skin property can be skin temperature, and each skin property measurement signal 58 can be a voltage signal that is proportional or otherwise related (e.g. via a lookup table) to the skin temperature within the sensing position of the skin temperature sensor.

If a skin contact sensor 64 is provided in the handheld device 2, the skin contact signal 62 may be a voltage signal that varies between high and low voltages (representing contact and no contact between the treatment end 7 or the aperture 6 and the skin).

The MCU 52 performs logical operations as described below, sends data to and receives data from the memory unit 56, and sends output signals to the output signal processing unit 54. The output signals sent to the output signal processing unit 54 can include a signal to control the energy source(s) 8 to trigger the generation of an energy pulse. The memory unit 56 stores data, such as the received digitised signals, information for use by the MCU 52 in processing the received digitised signals to determine whether to trigger an energy pulse, the number of energy pulses generated during the treatment operation, etc. The memory unit 56 can be in any of the forms described above.

The output signal processing unit 54 receives signals from the MCU 52, and sends an output signal 66 to the energy source(s) 8 to trigger the generation of an energy pulse. The output signal 66 is also referred to herein as 'pulse trigger signal 66', as it triggers the energy source(s) 8 to generate an energy pulse. Optionally, the MCU 52 and output signal processing unit 54 can output a user indicator signal 68 that indicates the status of the treatment operation to the user (or subject), for example indicating whether the treatment operation is complete. The user indicator signal 68 may be used to control or drive a user interface component, such as a light, display screen, loudspeaker or tactile (e.g. vibrating) element.

As noted above, the handheld device 2 according to the embodiments described herein provides for selective application of energy pulses to avoid treating skin areas that have already been adequately treated. This selective application of energy pulses is based on measurements of the skin property, since those measurements can indicate which parts of the skin have already been treated during this treatment operation. Since the control unit 10 can automatically identify the parts of the skin that have/have not been treated using the skin property measurements and trigger the energy pulses at the appropriate time, the user of the handheld device 2 is able to move the handheld device 2 over the skin area to be treated using a continuous motion, similar to when using other types of devices, such as shavers or razors, and achieve good coverage for the treatment. It will be appreciated that as the triggering of the energy pulses is based on detecting skin areas that have not been adequately treated, the motion does not have to be at a continuous speed and/or in a single direction, so it is possible for the user to move the handheld device 2 over the part of the body to be treated (e.g. a leg) with multiple passes or strokes (e.g. moving the handheld device 2 up and down the leg over the same areas of skin) with variable speed.

Briefly, to achieve this automatic mode of operation, the control unit 10 is configured to analyse the skin property measurements for the front sensing position 24 as the handheld device 2 is moved across the skin to identify whether an energy pulse has previously or recently been applied to the skin (e.g. if the skin still has a higher temperature following a previous energy pulse in the case where the skin property sensors measure skin temperature). Based on this information, the control unit 10 determines whether an energy pulse can be applied to the skin in the current skin treatment region 22. On detecting previously treated skin, pulsing is interrupted and based on analysis of the measurements from the front skin property sensor 14 and the back skin property sensor 16 and the known spatial relationship between the position of the back skin property sensor 16 and the treatment region, the control unit 10 determines an optimal moment for triggering the next pulse, thus optimising coverage. An amount of overlap between treatment regions can be controlled based on the known spatial relationship between at least the sensing position 26 that is behind the current skin treatment region 22 and the aperture 6.

In particular, the control unit 10 can analyse the skin property measurement signal from the front skin property sensor (e.g. the first skin property sensor 14 when the handheld device 2 is moved in direction 28) to identify areas of skin 17 that energy pulses have previously or recently been applied to. On identifying such an area of skin 17, the control unit 10 stores, records or logs the profile of the skin property measurements relating to the previously treated area of skin, or stores, records or logs an aspect of the profile of the skin property measurements (e.g. a maximum value, a minimum value, etc.) relating to the previously treated area of skin. The control unit 10 then analyses the skin property measurement signal from the back skin property sensor (e.g. the second skin property sensor 16 when the handheld device 2 is moved in direction 28) to identify the same previously treated area of skin (e.g. by identifying the same or similar measurement profile in the skin property measurement signal from the back skin property sensor). Once the control unit 10 makes that identification, the control unit 10 can determine that an energy pulse can be triggered (as the aperture 6 has passed over that previously-treated area of skin), provided that the minimum pulse repetition period for the energy source(s) 8 following the generation of a previous energy pulse has expired.

Some embodiments of the analysis and processing of the skin property measurements by the control unit 10 to achieve the automatic mode of operation are described below. Several of the embodiments are described with reference to the skin property being skin temperature and the energy pulse being a light pulse that performs the treatment operation but temporarily heats the skin where the light pulse is applied, but it will be appreciated that the embodiments described below can be applied where the skin property is a property other than skin temperature and/or where a different type of energy pulse is used.

The plots in FIG. 7 show exemplary skin temperature measurement signals obtained using the skin property sensor arrangement shown in FIG. 5, i.e. with the first skin temperature sensor 14 being in front of the aperture 6 (with respect to the direction of movement), and with the second skin temperature sensor 16 being behind the aperture 6 (with respect to the direction of movement).

Thus, FIG. 7(a) shows the temperature measurement signals from the two sensors 14 and 16 as the handheld device 2 is repeatedly moved over an area of skin that has previously been treated with an energy pulse. In particular, the handheld device 2 is moved over the treated area of skin in a first direction (e.g. a stroke down the leg) and then either repositioned back to the starting position and moved over the treated area of skin again in the same direction (e.g. another stroke down the leg) or after completing a stroke the handheld device 2 is turned around so that the first skin property sensor 14 remains in front of the aperture 6 and the handheld device 2 is moved over the treated area of skin in the opposite direction (e.g. a stroke up the leg).

Signal 80 is the temperature measurement signal from the first skin temperature sensor 14 and signal 82 is the temperature measurement signal from the second skin temperature sensor 16. It can be seen that there are several peaks in signals 80 and 82, which correspond to the skin in the sensing position of the respective skin temperature sensors having been recently treated with an energy pulse. The peaks in signal 80 occur earlier in time than the peaks in signal 82 as the first skin temperature sensor 14 (signal 80) encounters the treated area of skin before the second skin temperature sensor 16 as the handheld device 2 is moved over the skin. The highlighted part 84 of the signals corresponds to a period of time during which the handheld device 2 passed over the treated area of skin (and in particular the handheld device 2 was over the treated area of skin between the two peaks in part 84). Likewise, the highlighted part 86 of the signals corresponds to a subsequent period of time during which the handheld device 2 again passes over the treated area of skin (and in particular the handheld device 2 was over the treated area of skin between the two peaks in part 86). It will be noted that the magnitude of the temperature peaks with respect to the surrounding temperatures decreases over time (i.e. the temperature peak decreases with each pass of the handheld device 2 over the treated area, and thus the magnitude of the peak provides an indication of how recently the energy pulse was applied to the skin (with a higher magnitude corresponding to the energy pulse being applied more recently than a lower magnitude)), which can be due to the previously-treated area cooling down over time. Both signal 80 and signal 82 include troughs that occur at the same time, and this corresponds to the handheld device 2 losing contact with the skin (e.g. when the handheld device 2 is repositioned at the end of a stroke), and the temperature sensors measuring ambient air temperature (which in this case was lower than skin temperature).

It will be noted from FIG. 7(a) that the skin temperature measurement signals 80, 82 suffer from background noise, the quality of skin contact, signal drift and from skin temperature variation (e.g. variations within the subject or variations from subject to subject). Where these issues exist, a simple peak detection method or thresholding method operating on the raw signals 80, 82 may not be effective in detecting previously or recently treated areas of skin due to the presence of additional peaks not related to the treatment, and/or drift in the measurements over time.

FIG. 7(b) shows the result of filtering signals 80 and 82 to remove the drift and low frequency noise. The filtering of signal 80 results in filtered signal 88 and the filtering of signal 82 results in filtered signal 90. It will be noted that the peaks corresponding to the previously or recently treated area of skin remain visible in the filtered signals 88, 90.

In accordance with the techniques described herein, the control unit 10 analyses signal 80 to identify peaks corresponding to a previously treated area, and, having done so, the control unit 10 analyses signal 82 to identify the same or a similar peak. Once the control unit 10 identifies the end of the previously treated area based on a similar peak (or peaks) in signal 82, the control unit 10 can trigger an energy pulse.

In more detail, using the threshold method or the peak detecting method on the measurement signal from the front skin property sensor 14 enables the control unit 10 to identify whether or not the area of skin that the aperture 6 is about to pass over has previously or recently been treated with an energy pulse. With this information, if the control unit 10 identifies from the measurement signal obtained by the front skin property sensor 14 that there is an area of skin that has previously or recently been treated with an energy pulse, then the control unit 10 should 'expect' that area of previously or recently treated skin to be detectable in the measurement signal obtained by the back skin property sensor 16 shortly afterwards (the exact timing will depend on the speed of movement of the handheld device 2). In addition, if the control unit 10 identifies from the measurement signal obtained by the front skin property sensor 14 that there is an area of skin that has previously or recently been treated with an energy pulse, then the control unit 10 should wait until the marked point for that area of previously or recently treated skin is detected in the measurement signal obtained by the back skin property sensor 16 before triggering an energy pulse (provided that the minimum pulse repetition period from the last energy pulse has expired and the energy source(s) 8 are ready to generate an energy pulse).

The flow chart in FIG. 8 illustrates the operations of the control unit 10 according to an exemplary embodiment in more detail. One or more of the steps of the flow chart can be performed by the control unit 10 or skin property sensors 14, 16 as appropriate. The control unit 10 may perform the one or more steps in response to executing computer program code, that can be stored on a computer readable medium, such as, for example, the memory unit 56.

In step 101, a skin property measurement signal is acquired or obtained from the front skin property sensor (which for the purposes of this flow chart is considered to be the first skin property sensor 14). This signal can be acquired or obtained generally continuously or periodically (e.g. according to a sampling period for the first skin property sensor 14). This signal is referred to as the front sensor measurement signal. A profile of the front sensor measurement signal can be stored in a memory unit, such as a buffer, as it is acquired. The memory unit may store a profile of the front sensor measurement signal of a predetermined length (e.g. the profile can be stored until the memory unit is full or the memory unit has otherwise stored a sufficiently long front sensor measurement signal profile), the oldest part(s) of the front sensor measurement signal profile stored in the memory unit can be discarded to make room for a newly acquired part of the profile of the front sensor measurements.

In step 103, a skin property measurement signal is acquired or obtained from the back skin property sensor (which for the purposes of this flow chart is considered to be the second skin property sensor 16). This signal can be acquired or obtained generally continuously or periodically (e.g. according to a sampling period for the second skin property sensor 16). This signal is referred to as the back sensor measurement signal. The back sensor measurement signal, and/or a profile of the back sensor measurement signal, can be stored in a memory unit (which can be the same or different to the memory unit that the profile of the front measurement signal is stored in), such as a buffer, as it is acquired. Once the memory unit has stored a profile of the back sensor measurement signal of a predetermined length (e.g. the profile can be stored until the memory unit is full or the memory unit has otherwise stored a sufficiently long back sensor measurement signal profile), the oldest part(s) of the back sensor measurement signal profile stored in the memory unit can be discarded to make room for a newly acquired part of the profile of the back sensor measurements.

Steps 101 and 103 occur at generally the same time.

Next, in step 105, the control unit 10 analyses the front sensor measurement signal profile. In particular step 105 can analyse the front sensor measurement signal stored in the memory unit. This step can include filtering the front sensor measurement signal profile to remove drift and/or noise. In addition or alternatively, this step can include filtering the front sensor measurement signal profile to remove global variations of the skin property (e.g. due to a change in the temperature of the environment).

In step 105, the front sensor measurement signal is analysed to determine if the front skin property sensor 14 is passing over a previously treated area of skin 17. In particular, step 105 can comprise determining if there is a peak in the measurement signal corresponding to a previously treated area of skin 17. In some embodiments, a simple thresholding method can be used to identify a previously or recently treated area of skin by finding a peak in the profile (comprising one or more consecutive measurements) that exceeds a threshold value (for example a threshold value derived with respect to a background level). The thresholding method could be used on the raw measurement signals (e.g. signals 80, 82 shown in FIG. 7) or signals that have been processed or filtered to correct for drift and/or noise (e.g. signals 88, 90 in FIG. 7). A typical value for the threshold could be a multiple (e.g. 3) of the standard deviation of the skin property measurement value above an average background level, although other threshold values can be used (and they can be derived in different ways).

In the above example, the idea is to have a score that represents 'the height' of the peak, but there are many alternative ways to analyse the profile of the first measurement signal to determine if the first skin property sensor is passing over a previously treated area of skin, like:

A score calculated from a selection of data points in the stored measurement signal aimed at representing the derivative of the signal (smoothed by filtering).

A score calculated from a Short Time Fourier Transform (STFT) of the stored measurement signal aimed at aimed at representing frequency components in a range corresponding to a typical peak in the measured skin property (these would be frequencies between slow global variations and high-frequency noise).

Similar as above, but using Continuous Wavelet Transform as an alternative to STFT.

At step 107 it is determined whether a peak is detected in the front sensor measurement signal. If not, then the control unit 10 can permit the triggering of an energy pulse (step 109). Whether an energy pulse is actually triggered depends on whether the minimum pulse repetition period since the last energy pulse has expired. If the minimum pulse repetition period has expired, the control unit 10 can trigger the energy pulse at this time. If the minimum pulse repetition period has not expired, the process can return to step 101/105 and the current profile of the front sensor measurement signal stored in the memory unit is analysed to determine if the front skin property sensor 14 is now passing over a previously treated area of skin 17 (as the handheld device 2 has moved since step 105 was previously performed). If the minimum pulse repetition period expires and still no previously treated area of skin 17 is detected, then an energy pulse can be triggered by the control unit 10.

If at step 107 a peak (or other evidence of a previously-treated area of skin 17) is detected in the front sensor measurement signal profile, then the control unit 10 prevents a pulse being triggered (step 111), as the aperture 6 is about to pass (or is already passing) over the previously treated area of skin 17. The control unit 10 can prevent the pulse being triggered by not sending a control signal to the energy source(s) 8 to trigger the generation of an energy pulse, or by sending a control signal to the energy source(s) 8 that indicates that an energy pulse should not be triggered at this time. Thus, even if the minimum pulse repetition period has expired, the control unit 10 prevents the energy pulse being triggered.

The control unit 10 then marks a point in the front sensor measurement signal profile according to a predetermined rule (step 113), and stores information about this point (e.g. the signal magnitude, or part of the profile of the measurement signal up to, following, and/or around this point). The marked point generally relates to a position on the previously treated area of skin. This information may be stored separately from the front sensor measurement signal profile itself, so it is not discarded from the memory unit by new measurements being acquired from the front skin property sensor 14. The predetermined rule can specify what the marked point is. For example the marked point can be a point corresponding to the peak measurement (i.e. the maximum), a point corresponding to the start of a peak (e.g. the last skin property measurement before the skin property measurement values started to increase towards the peak), a point corresponding to the end of a peak (e.g. the first skin property measurement at an untreated level after the peak), some intermediate point (e.g. between the peak and the start or end of the peak) or a point corresponding to an end peak in a series of peaks (e.g. representing several closely-spaced previous treatment areas). The intermediate point could be, for example, halfway between the peak and the point at the end of the peak, but other positions could be used.

As described in more detail below, the predetermined rule, along with the specific spacing of the back skin property sensor 14, 16 from the aperture 6, determines the degree of overlap (or not) with the previously treated area of skin. The predetermined rule can be preset and fixed for the handheld device 2 (for example it can be determined during manufacture) so that the amount of overlap cannot be changed. Alternatively, the predetermined rule can be set by a user of the handheld device 2, for example based on a desired treatment level (e.g. more overlap would lead to more energy being applied to the skin over the course of the treatment operation, and vice versa). Alternatively, the predetermined rule can be set and/or adjusted during the treatment operation by the handheld device 2 based on characteristics of the skin being treated. For example, the handheld device 2 can determine a response of the skin to the energy pulse (e.g. by analysis of the sensor measurement signal(s)), and adjust the amount of overlap permitted based on that response. For example, if the skin responds strongly to energy pulses, then the predetermined rule can be adjusted to reduce the degree of overlap (and vice versa).

Next, in step 115, the stored information about the marked point in the front sensor measurement signal profile is compared to the back sensor measurement signal profile. This step aims to identify the same or similar point in the back sensor measurement signal profile (e.g. the same peak value, the same position on a peak, the same signal/measurement profile, etc.), which would indicate that the position (and thus the required amount of the previously treated area of skin 17) has passed through the aperture 6. Step 115 can comprise analysing the back sensor measurement signal profile to identify previously treated areas of skin in the same way as analysing the first sensor measurement signal profile in step 105, and, having detected a previously treated area of skin in the back sensor measurement signal profile, step 115 can comprise determining if a point corresponding to the marked point can be identified.

Once that point is identified in the back sensor measurement signal point, the control unit 10 can permit the triggering of an energy pulse (step 117), subject to expiry of the minimum pulse repetition period for the energy source(s) 14 (as above for step 109). The process can then return to step 101/105 and repeat for the current front sensor measurement profile stored in the memory unit.

Figure 9:
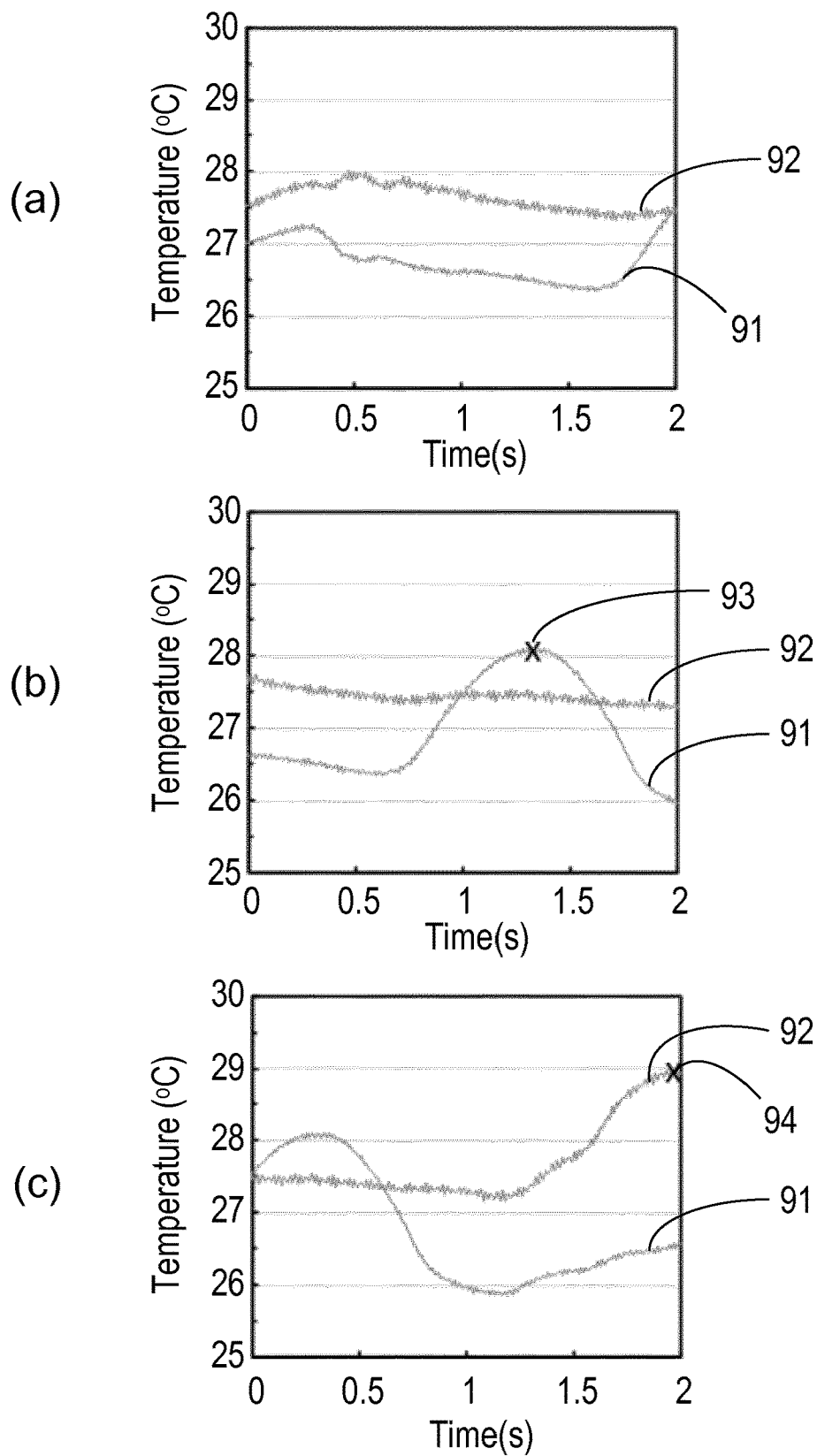
FIG. 9 shows exemplary sets of temperature measurements from a front skin temperature sensor and a back skin temperature sensor.

The operation of the control unit set out in FIG. 8 will now be described with reference to the graphs in FIG. 9. The graphs in FIG. 9 show skin temperature measurements obtained using a front skin property sensor 14 and a back skin property sensor 16 that are each spaced 5 mm from the respective nearest edge of the aperture 6, with the aperture 6 having a width of 10 mm. It will be noted that the measurements from the back skin property sensor 16 are consistently about 1° higher than the corresponding measurements from the front skin property sensor 14. This just down to calibration differences between the sensors used to obtain these measurements. The front skin property sensor 14 and the back skin property sensor 16 are positioned as shown in FIG. 4. FIG. 9 includes three graphs (FIGS. 9(*a*), 9(*b*) and 9(*c*)) that show measurement signal profiles for each sensor 14, 16 obtained from a skin phantom that has previously been irradiated with a single flash. The measurement profiles shown in each graph are the measurement profiles stored in a memory unit for each skin property sensor 14, 16 at three different time points as the handheld device 2 is moved over the skin phantom. In this example, the memory unit stores 2 seconds worth of measurement profile from each sensor 14, 16. In FIG. 9, the measurement profile from the front skin property sensor 14 is denoted signal/profile 91 and the measurement profile from the back skin property sensor 16 is denoted signal/profile 92.

In FIG. 9(*a*) the front skin property sensor 14 is approaching the irradiated region, and the start of the peak due to the previous flash can be seen on the right side of the signal/profile 91. The temperature measured at the back skin property sensor 16 is generally constant in this set of measurements/profile 92.

In FIG. 9(*b*) the front skin property sensor 14 is passing over the previously treated skin area and so a temperature peak is shown in the front sensor measurement profile 91, but the temperature measured at the back skin property sensor 16 remains generally constant. According to step 105/107 of FIG. 8, the treated area of skin is identified in the measurement profile in FIG. 9(*b*) and pulses are prevented. Further analysis of the front measurement profile 91 in FIG. 9(*b*) also indicates that the front skin property sensor 14 has passed the peak (since the most recent temperature measurements by the front skin property sensor 14 indicate that the temperature is back to a background level). In this example the peak itself is marked (indicated by point 93, step 113 in FIG. 8). Information about the peak, for example the value of the peak temperature, the duration of the peak, the profile of the temperature change at or around the peak, etc., is stored.

The control unit 10 then analyses the back measurement signal profile 92 to identify the same peak at the back skin property sensor 16 (step 115). In FIG. 9(*c*), it can be seen from the back sensor measurement signal profile 92 that the back skin property sensor 16 has arrived at the location of the temperature peak (noted by peak 94). Therefore, at this time, the control unit 10 can determine that the aperture 6 has passed over the previously treated area, and another pulse can be triggered.

Triggering a new flash when the back skin property sensor 16 is at the temperature maximum of the previous treatment region means that the next flash is triggered when the back skin property sensor 16 is centred on the previous treatment region. With the back skin property sensor 16 being spaced 5 mm from the 10 mm-wide aperture 6, this operation means that there is no overlap (and minimal gap) between the previously treated area and the current skin treatment region 22.

Figure 10:
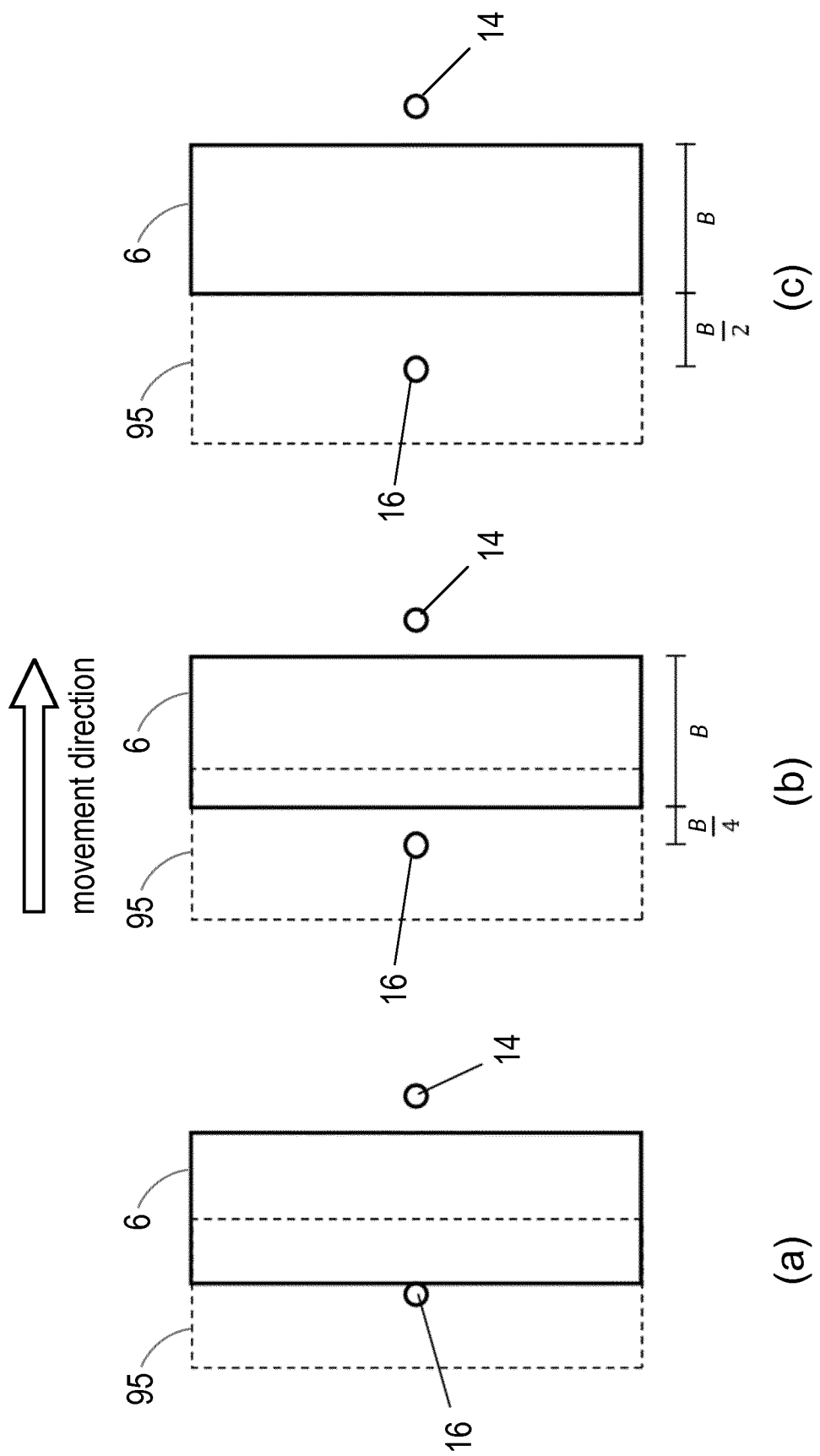
FIG. 10 illustrates how the position of a back skin property sensor affects an amount of overlap between treatment areas.

As noted above, the overlap of a new treatment region (where an energy pulse is to be applied), can be determined by the position of the back skin property sensor 16 with respect to the aperture 6, and the predetermined rule used to mark a position in the profile relating to the previously treated region of skin. The effect of the position of the back skin property sensor 16 on the overlap is illustrated in FIG. 10, with the marked point being the peak value and the control unit 10 triggering the next pulse as soon as the peak value is detected at the back skin property sensor 16. FIG. 10 illustrates three different positions of the back skin property sensor 16 with respect to the aperture 6, and dashed box 95 is an outline of a previously treated area of skin. In FIG. 10(*a*) the back skin property sensor 16 is positioned adjacent to the aperture 6, and so the overlap will be around 50%. If the back skin property sensor 16 is placed at a distance B/4 from the edge (where B is the width of the aperture 6 in the direction of movement—as in FIG. 4), the overlap will be around 25%. If the back skin property sensor 16 is placed at a distance B/2 from the edge of the aperture 6, the overlap will be 0%, i.e. the new and previous treatment regions will be adjacent.

For good correspondence of the measurement signals/profiles from the front skin property sensor 14 and the back skin property sensor 16, the sensors 14, 16 should be arranged on the same single line parallel to the movement direction (e.g. as shown in FIG. 4). Typically, this is a line parallel to the narrow edges of the aperture 6. It will be noted that the position of the front skin property sensor 14 with respect to the edge of the aperture 6 does not directly affect the amount of overlap. However, to enable the handheld device 2 to be used is either movement direction (e.g. in direction 28 or the opposite direction) with the same treatment effects (i.e. the same amount of overlap), the front skin property sensor 14 and the back skin property sensor 16 should be spaced from the aperture 6 by the same amount.

Figure 11:
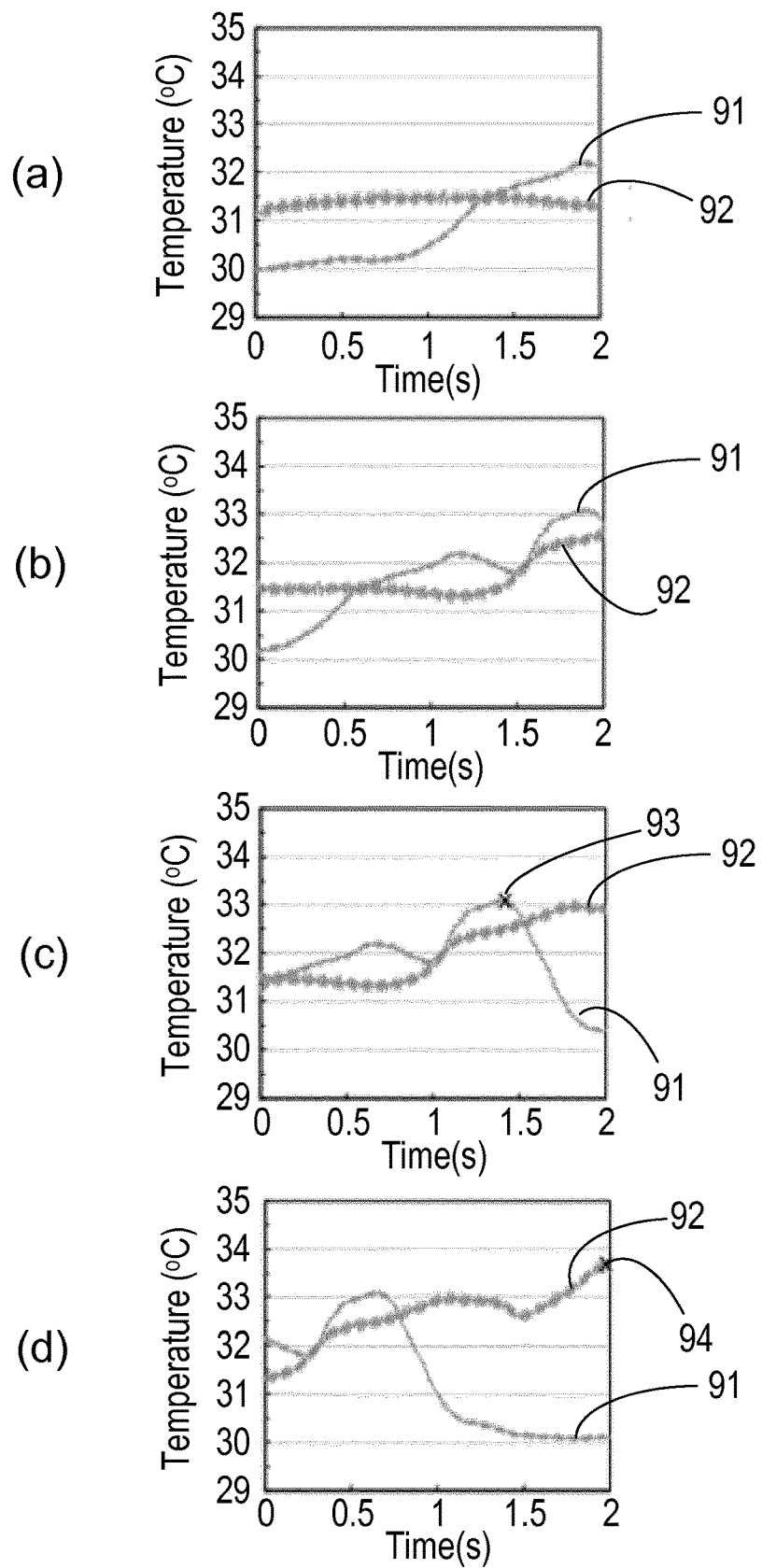
FIG. 11 shows other exemplary sets of temperature measurements from a front skin temperature sensor and a back skin temperature sensor.

In the example shown in FIG. 9, the skin had only been treated with a single flash. The graphs in FIG. 11 show skin temperature measurement profiles obtained using a front skin property sensor 14 and a back skin property sensor 16 that are each spaced 5 mm from the respective nearest edge of the aperture 6, with the aperture 6 having a width of 10 mm (the same as for FIG. 9), where three separate flashes have been administered to the skin (of a human volunteer) in consecutive previous passes. It should be noted that in this example the temperature signatures/profiles of these previous flashes are overlapping (i.e. there was overlap between the treatment regions). In FIG. 11(*a*) the signal/profile 91 from the front skin property sensor 14 suggests that the maximum of a temperature peak may have just been passed. However, after the handheld device 2 has been moved a little further, the signal/profile 91 stored in the memory unit shows that there is a further adjacent peak (FIG. 11(*b*)). FIG. 11(*c*) shows the skin temperature profile after the handheld device 2 has moved still further. From the signal/profile 91, the control unit 10 can now determine that the end of the previous treatment region(s) has passed and the temperature is back to a background signal. The maximum corresponding to the last peak in the signal/profile 91 from the front skin property sensor 14 is marked (indicated by point 93). According to the method, the signal/profile 92 from the back skin property sensor 16 is then analysed to identify that same point. In FIG. 11(*d*), it can be seen that the back skin property sensor 16 has arrived at the location of this maximum (indicated by point 94). The algorithm recognises the previously marked point 94 in the signal/profile 92 from the back skin property sensor 16, and the control unit 10 enables the triggering of another flash.

As noted above, the handheld device 2 includes one or more energy sources 8. In some embodiments, the handheld device 2 includes a plurality of energy sources 8 (e.g. a plurality of LEDs), and the plurality of energy sources 8 are spatially distributed so that each energy source 8 applies an energy pulse to a particular part or region of the skin in the current skin treatment region 22. Furthermore, one or more of the plurality of energy sources 8 can be controlled by the control unit 10 to generate energy pulses independently of the other energy sources 8, which means that the control unit 10 is able to provide energy pulses to only a part of the skin in the current skin treatment region 22 when an energy pulse is to be generated. This individual control of the triggering of the energy sources 8 (which is also referred to as individual addressability of the energy sources 8) may be useful for filling in the gaps between previously treated areas of skin where the gap is smaller than the size of the aperture 6/current skin treatment region 22.

There are two main ways in which this individual control can be implemented. These control techniques can be used separately or in combination. In the first way, the individual control can allow for longitudinal addressability of the energy sources 8. In the longitudinal addressability, the energy sources are arranged in series with respect to the intended direction of movement (i.e. when the handheld device 2 is being moved in the intended direction of movement, the energy sources pass over a particular point of skin in turn), which means that the size of the area of skin in the current skin treatment region 22 that is directly exposed to an energy pulse can be tuned in the direction similar to the direction of motion of the handheld device 2 (in other words the width of the current skin treatment region 22 can be reduced (or increased) by triggering one or more of the energy sources at a particular time). In this way, if the analysis of the skin property measurement signal/profile(s) by the control unit 10 identifies a gap between two previously treated areas that is smaller than the size of a full skin treatment region 22, then the control unit 10 can control only some of the energy sources 8 to generate an energy pulse to only treat the skin in the gap.

A further option with this longitudinal addressability is that, if the control unit 10 has identified an area of the skin that an energy pulse is to be applied to (whether or not that area is a gap between two previously treated areas that is smaller than the size of a full skin treatment region 22) and the control unit 10 has information on the speed of motion of the handheld device 2 (e.g. from a motion sensor in the handheld device 2, such as an accelerometer or an optical sensor), the control unit 10 may trigger the energy sources 8 sequentially (e.g. starting with the energy source 8 closest to the 'front' of the handheld device 2) to keep that area of skin exposed to the light while the handheld device 2 moves over it. In this way, the longitudinally-addressable energy sources 8 can be controlled to apply several energy pulses to a particular (smaller) area of skin during a single pass over that area of skin.

The second way in which individual control can be used is to allow orthogonal addressability of the energy sources 8. The use of orthogonal addressability can be used to overcome problems with having to locate the skin property sensors 14, 16 some distance from the aperture 6/current skin treatment region 22 (e.g. B or B/2 according to the embodiment in FIG. 4), which would mean a larger head size.

Figure 12:
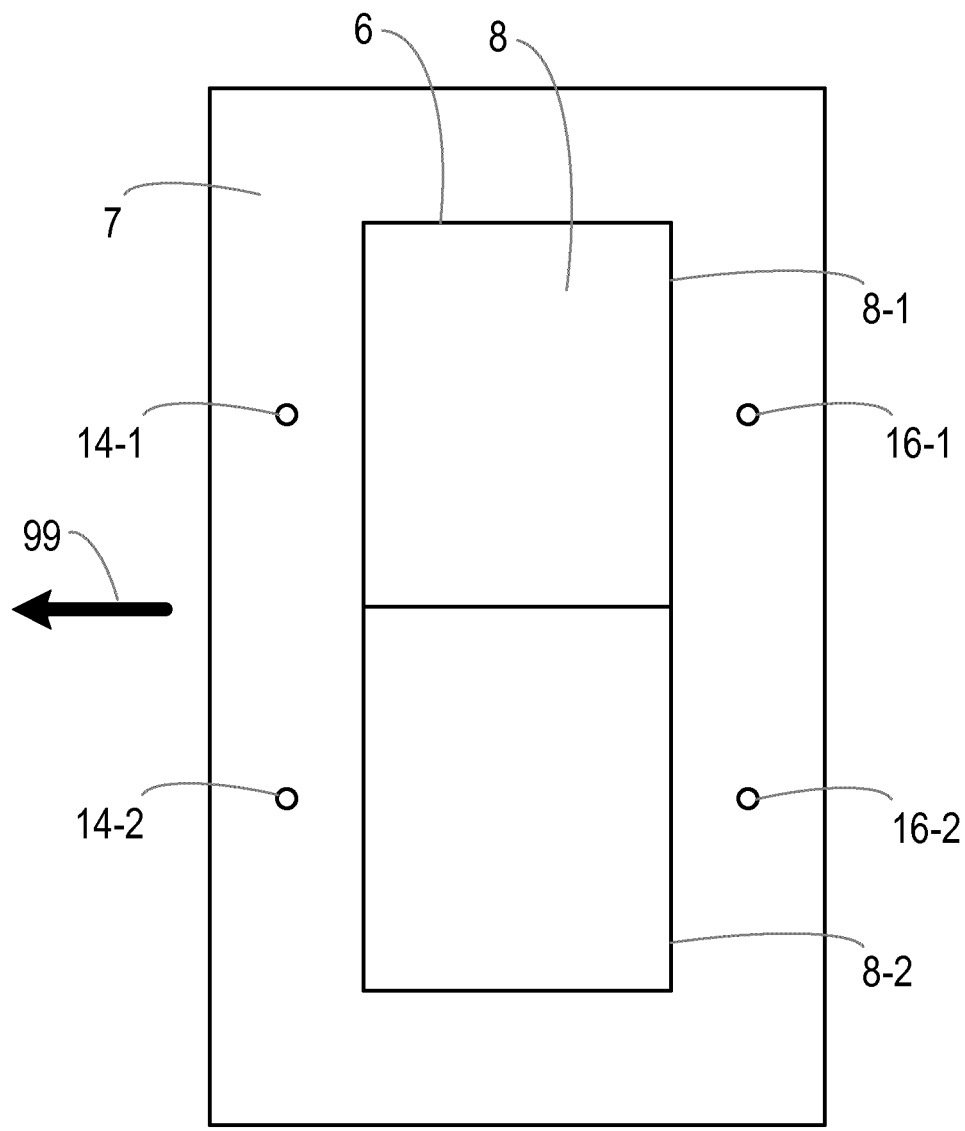
FIG. 12 shows an exemplary arrangement of energy sources and skin property sensors in which orthogonal addressability can be used.

FIG. 12 shows an exemplary arrangement of energy sources 8 and skin property sensors 14, 16 in which orthogonal addressability can be used. In particular, FIG. 12 shows a treatment end 7 having aperture 6 and a plurality of energy sources 8. The energy sources 8 comprise first energy source(s) 8-1 and second energy source(s) 8-2 that can be individually controlled by the control unit 10 to generate energy pulses (although it will be appreciated that the energy sources 8 may comprise more than two energy sources 8 or more than two groups of energy sources 8 that can be individually controlled). The energy sources 8 are arranged in parallel with respect to the intended motion direction (indicated by arrow 99), i.e. the energy sources are side-by-side. The energy sources 8 may be an array of LEDs. Four skin property sensors 14, 16 are arranged around the aperture 6, with respective skin property sensors 14, 16 provided 'in front' and 'behind' the first energy source(s) 8-1 (which are denoted 14-1 and 16-1 respectively) and respective skin property sensors 14, 16 provided 'in front' and 'behind' the second energy source(s) 8-2 (which are denoted 14-2 and 16-2 respectively) with respect to an intended motion direction 99. In the example of FIG. 12, each skin property sensor 14-1, 14-2, 16-1, 16-2 is positioned at or around the midpoint of the length of the respective energy source(s) 8-1, 8-2. It will be appreciated that in other implementations more than four skin property sensors can be used, for example depending on the number of groups of energy sources 8. In this exemplary arrangement, the control unit 10 can process or analyse the measurement signals/profiles from each pair of the skin property sensors 14, 16 (i.e. 14-1 and 16-1 or 14-2 and 16-2) as described above with respect to FIG. 8 to determine whether the respective energy source(s) 8-1, 8-2 should be triggered. That is, the flow chart of FIG. 8 can be performed for the measurement signals/profiles from front skin property sensor 14-1 and back skin property sensor 16-1 to determine whether energy source(s) 8-1 can be triggered, and the flow chart can be performed for the measurement signals/profiles from front skin property sensor 14-2 and back skin property sensor 16-2 to determine whether energy source(s) 8-2 can be triggered. As with the other embodiments described above, the distance between the back skin property sensors 16-1, 16-2 and the respective energy source(s) 8-1, 8-2 can be set based an amount of overlap that is desired between skin treatment regions.

In some embodiments, the control unit 10 can use information relating to the detection of a peak in the skin property measured by a front skin property sensor 14 and the subsequent detection of a peak in a back skin property sensor 16 and information on the distance between the front skin property sensor 14 and back skin property sensor 16 to determine the displacement of the handheld device 2. In some embodiments, the control unit 10 can use information relating to the timing of the detection of a peak in the skin property measured by a front skin property sensor 14 and the timing of the subsequent detection of the peak in a back skin property sensor 16 and information on the distance between the front skin property sensor 14 and back skin property sensor 16 to determine the speed of movement of the handheld device 2.

In some embodiments, the control unit 10 can determine feedback for the user on the use of the handheld device 2 based on the determined information on the speed and/or displacement of the handheld device 2. The feedback may be, for example, that the user should move the handheld device 2 more slowly or more quickly to improve the efficiency of the overall treatment operation.

There is therefore provided various handheld devices to perform treatment operations on skin using energy pulses that can enable a user to complete the treatment operation in an efficient and effective manner.

Variations to the disclosed embodiments can be understood and effected by those skilled in the art in practicing the principles and techniques described herein, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A handheld device for applying energy pulses to skin of a subject to perform a treatment operation as the handheld device is moved across the skin, the handheld device comprising:
   an aperture that is to be placed adjacent to the skin,
   at least one energy source for generating energy pulses and for providing the energy pulses through the aperture to perform the treatment operation on skin adjacent the aperture, wherein the at least one energy source has a minimum pulse repetition period following the generation of an energy pulse before a subsequent energy pulse can be generated;
   a first skin property sensor for measuring a skin property and for outputting a first measurement signal representing measurements of the skin property at a first sensing position, wherein the skin property is a property that changes in response to application of an energy pulse to the skin, and wherein the first sensing position is in front of the aperture relative to an intended motion direction of the handheld device over the skin;
   a second skin property sensor for measuring the skin property and for outputting a second measurement signal representing measurements of the skin property at a second sensing position, wherein the second sensing position is behind the aperture relative to the intended motion direction, and wherein each of the first skin property sensor and the second skin property sensor is a temperature sensor, an optical sensor, an acoustic sensor or an electrical sensor;
   a memory unit; and
   a control unit that is coupled to the at least one energy source to control the generation of the energy pulses by the at least one energy source, and coupled to the first skin property sensor and the second skin property sensor to obtain the first measurement signal and the second measurement signal, respectively, wherein the control unit is configured to store a profile of at least the first measurement signal in the memory unit;
   wherein the control unit is further configured to, when the handheld device is moving in the intended motion direction over the skin:
      analyze the profile of the first measurement signal to determine if the first skin property sensor is passing over a previously treated area of skin;
      on detecting that the first skin property sensor is not passing over a previously treated area of skin, control the at least one energy source to generate an energy pulse when the minimum pulse repetition period following generation of a previous energy pulse has expired;
      on detecting that the first skin property sensor is passing over a previously treated area of skin, perform consecutive operations comprising:
         preventing generation of an energy pulse, even if the minimum pulse repetition period following the generation of a previous energy pulse has expired;
         marking a point in the profile of the first measurement signal stored in the memory unit, wherein the marked point relates to a position on the previously treated area of skin;
         using information about the marked point, analyze a profile of the second measurement signal to identify a similar marked point in the profile of the second measurement signal; and
         on identifying the similar marked point in the profile of the second measurement signal, controlling the at least one energy source to generate an energy pulse when the minimum pulse repetition period following the generation of the previous energy pulse has expired.

2. The handheld device as claimed in claim 1, wherein the aperture has a width that is a dimension of the aperture measured in a plane of the aperture and measured parallel to the intended motion direction, wherein each of the first skin property sensor and the second skin property sensor spaced from respective edges of the aperture by respective distances that are equal to or less than the width.

3. The handheld device as claimed in claim 1, wherein the profile of the first measurement signal stored in the memory unit comprises measurements of the skin property at the first sensing position most recently obtained from the first skin property sensor, and the profile of the second measurement signal stored in the memory unit comprises measurements of the skin property at the second sensing position most recently obtained from the second skin property sensor.

4. The handheld device as claimed in claim 1, wherein the control unit is configured to analyze the profile of the first measurement signal to determine if the first skin property sensor is passing over a previously treated area of skin by:
comparing the measurements in the profile of the first measurement signal to a threshold value, and
determining that the first skin property sensor is passing over a previously treated area of skin when one or more consecutive measurements exceed the threshold value.

5. The handheld device as claimed in claim 1, wherein the marked point is:
a point corresponding to a peak in the profile of the first measurement signal,
a point corresponding to a start of a peak in the profile of the first measurement signal,
a point corresponding to an end of a peak in the profile of the first measurement signal, or
a point between a peak in the profile of the first measurement signal and a start or an end of the peak.

6. The handheld device as claimed in claim 1, wherein the control unit is further configured to:
an amount of overlap between a previously treated area of skin and skin adjacent the aperture when an energy pulse is to be generated following the identification of the similar marked point in the profile of the second measurement signal.

7. The handheld device as claimed in claim 1, wherein the information about the marked point indicates at least one:
a value of the first measurement signal at the marked point,
a position of the marked point with respect to the previously treated area of skin, or
a partial profile of the measurements at and/or around the marked point in the first measurement signal.

8. The handheld device as claimed in claim 1, wherein the control unit is configured to analyze the profile of the second measurement signal to identify the similar marked point in the previously treated area of skin by:
analyzing the profile of the second measurement signal to determine if the second skin property sensor is passing over a previously treated area of skin; and
on detecting that the second skin property sensor is passing over a previously treated area of skin, using the information about the marked point to identify the similar marked point in the profile of the second measurement signal.

9. The handheld device as claimed in claim 1, wherein the control unit is further configured to:
determine a direction in which the handheld device is moving over the skin.

10. The handheld device as claimed in claim 9, wherein the control unit is configured to determine the direction in which the handheld device is moving over the skin by:
analyzing the profile of the first measurement signal and the profile of the second measurement signal to identify corresponding signal features in the profile of the first measurement signal and the profile of the second measurement signal; and
determining the direction in which the handheld device is moving from relative timings of the corresponding signal features in the profile of the first measurement signal and the profile of the second measurement signal.

11. The handheld device as claimed in claim 9, wherein the handheld device further comprises a movement sensor for measuring a movement of the handheld device and outputting a movement measurement signal to the control unit, and wherein the control unit is configured to determine the direction in which the handheld device is moving over the skin by analyzing the movement measurement signal.

12. The handheld device as claimed in claim 1, wherein the control unit is further configured to filter the first and second measurement signals to remove drift and/or noise.

13. The handheld device as claimed in claim 1, wherein the at least one energy source comprises a first energy source and a second energy source that are separately controllable by the control unit, and wherein the first energy source and the second energy source are arranged in the handheld device in series with respect to the intended motion direction.

14. The handheld device as claimed in claim 1,
wherein the at least one energy source comprises a first energy source and a second energy source that are separately controllable by the control unit, and wherein the first energy source and the second energy source are arranged in the handheld device in parallel with respect to the intended motion direction;
wherein the first sensing position is in front of the first energy source relative to the intended motion direction, and the second sensing position is behind the first energy source relative to the intended motion direction;
wherein the handheld device further comprises:
a third skin property sensor for measuring the skin property and for outputting a third measurement signal representing measurements of the skin property at a third sensing position as the handheld device is moved across the skin, wherein the third sensing position is in front of the second energy source relative to the intended motion direction;
a fourth skin property sensor for measuring the skin property and for outputting a fourth measurement signal representing measurements of the skin property at a fourth sensing position as the handheld device is moved across the skin, wherein the fourth sensing position is behind the second energy source relative to the intended motion direction wherein each of the third skin property sensor and the fourth skin property sensor is a temperature sensor, an optical sensor, an acoustic sensor or an electrical sensor; and
the control unit is configured to analyze the first measurement signal and the second measurement signal to determine whether an energy pulse can be generated by the first energy source, and to analyze the third measurement signal and the fourth measurement signal to determine whether an energy pulse can be generated by the second energy source.

15. A non-transitory computer readable medium having computer readable code embodied therein, the computer readable code being configured for execution by a control unit in a handheld device, wherein the handheld device comprises:
an aperture that is to be placed adjacent to skin of a subject;
at least one energy source for generating energy pulses and for providing the energy pulses through the aperture to perform a treatment operation on skin adjacent the aperture, wherein the at least one energy source has a minimum pulse repetition period following the generation of an energy pulse before a subsequent energy pulse can be generated;
a first skin property sensor for measuring a skin property and for outputting a first measurement signal representing measurements of the skin property at a first sensing position, wherein the skin property is a property that changes in response to application of an energy pulse to the skin, and wherein the first sensing position is in front of the aperture relative to an intended motion direction of the handheld device over the skin;
a second skin property sensor for measuring the skin property and for outputting a second measurement signal representing measurements of the skin property at a second sensing position, wherein the second sensing position is behind the aperture relative to the intended motion direction, and wherein each of the first skin property sensor and the second skin property sensor is a temperature sensor, an optical sensor, an acoustic sensor or an electrical sensor; and
a memory unit;
wherein the control unit is coupled to the at least one energy source to control the generation of the energy pulses by the at least one energy source, and coupled to the first skin property sensor and the second skin property sensor to obtain the first measurement signal and the second measurement signal, wherein the control unit is configured to store a profile of at least the first measurement signal in the memory unit; and
wherein, on execution of the computer readable code by the control unit, the control unit is caused to, when the handheld device is moving in the intended motion direction over the skin:
analyze the profile of the first measurement signal to determine if the first skin property sensor is passing over a previously treated area of skin;
on detecting that the first skin property sensor is not passing over a previously treated area of skin, control the at least one energy source to generate an energy pulse when the minimum pulse repetition period following the generation of a previous energy pulse has expired;
on detecting that the first skin property sensor is passing over a previously treated area of skin, perform consecutive operations comprising:
preventing generation of an energy pulse, even if the minimum pulse repetition period following the generation of a previous energy pulse has expired;
marking a point in the profile of the first measurement signal stored in the memory unit, wherein the marked point relates to a position on the previously treated area of skin;
using information about the marked point, analyze a profile of the second measurement signal to identify a similar marked point in the profile of the second measurement signal; and
on identifying the similar marked point in the profile of the second measurement signal, controlling the at least one energy source to generate an energy pulse when the minimum pulse repetition period following the generation of the previous energy pulse has expired.

16. A handheld device for applying energy pulses to skin of a subject to perform a treatment operation as the handheld device is moved across the skin, the handheld device comprising:
an aperture that is to be placed adjacent to the skin;
means for generating energy pulses and for providing the energy pulses through the aperture to perform the treatment operation on skin adjacent the aperture, wherein the means for generating energy pulses has a minimum pulse repetition period following generation of an energy pulse before a subsequent energy pulse can be generated;
first means for measuring a skin property and for outputting a first measurement signal representing measurements of the skin property at a first sensing position, wherein the skin property is a property that changes in response to application of an energy pulse to the skin, and wherein the first means for measuring the skin property is positioned in front of the aperture relative to an intended motion direction of the handheld device over the skin;
second means for measuring the skin property and for outputting a second measurement signal representing measurements of the skin property at a second sensing position, wherein the second sensing position is behind the aperture relative to the intended motion direction;
a memory unit; and
means for controlling operation of the handheld device configured to control the first means for measuring the skin property to obtain the first measurement signal, to control the second means for measuring the skin property to obtain the second measurement signal, and to store a profile of at least the first measurement signal in the memory unit;
wherein, when the handheld device is moving in the intended motion direction over the skin, the means for controlling operation of the handheld device is further configured to:
analyze the profile of the first measurement signal to determine when the first means for measuring the skin property is passing over a previously treated area of skin;
on detecting that the first means for measuring the skin property is not passing over a previously treated area of skin, control the means for generating the energy pulses to generate an energy pulse when the minimum pulse repetition period following generation of a previous energy pulse has expired;
on detecting that the first means for measuring the skin property is passing over a previously treated area of skin, perform consecutive operations comprising:
preventing generation of an energy pulse, even when the minimum pulse repetition period following the generation of a previous energy pulse has expired;
marking a point in the profile of the first measurement signal, wherein the marked point relates to a position on the previously treated area of skin;
using information about the marked point, analyze a profile of the second measurement signal to identify a similar marked point in the profile of the second measurement signal; and
on identifying the similar marked point in the profile of the second measurement signal, controlling the at least one energy source to generate an energy pulse when the minimum pulse repetition period following the generation of the previous energy pulse has expired.

17. The handheld device as claimed in claim 16, wherein the aperture has a width that is a dimension of the aperture measured in a plane of the aperture and measured parallel to the intended motion direction, wherein each of the first and second means for measuring the skin property is spaced from respective edges of the aperture by respective distances that are equal to or less than the width.

18. The handheld device as claimed in claim 16, wherein the profile of the first measurement signal stored in the memory unit comprises measurements of the skin property at the first sensing position most recently obtained from the first means for measuring the skin property, and the profile of the second measurement signal comprises measurements of the skin property at the second sensing position most recently obtained from the second means for measuring the skin property.

19. The handheld device as claimed in claim 16, wherein the means for controlling operation of the handheld device is configured to analyze the profile of the first measurement signal to determine when the first means for measuring the skin property is passing over a previously treated area of skin by:
- comparing the measurements in the profile of the first measurement signal to a threshold value; and
- determining that the first means for measuring the skin property is passing over a previously treated area of skin when one or more consecutive measurements exceed the threshold value.

20. The handheld device as claimed in claim 16, wherein the marked point is:
- a point corresponding to a peak in the profile of the first measurement signal,
- a point corresponding to a start of a peak in the profile of the first measurement signal,
- a point corresponding to an end of a peak in the profile of the first measurement signal, or
- a point between a peak in the profile of the first measurement signal and a start or an end of the peak.

* * * * *